United States Patent
Zhang

(10) Patent No.: US 11,911,467 B2
(45) Date of Patent: *Feb. 27, 2024

(54) COMPOSITION COMPRISING PIC FOR TREATMENT OF CANCER

(71) Applicant: Yisheng Biopharma (Singapore) PTE LTD, Singapore (SG)

(72) Inventor: Yi Zhang, Singapore (SG)

(73) Assignee: YISHENG BIOPHARMA (SINGAPORE) PTE LTD, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 17/833,133

(22) Filed: Jun. 6, 2022

(65) Prior Publication Data

US 2023/0051846 A1    Feb. 16, 2023

Related U.S. Application Data

(63) Continuation of application No. 16/085,944, filed as application No. PCT/SG2017/050179 on Mar. 31, 2017, now Pat. No. 11,382,972.

(30) Foreign Application Priority Data

Apr. 1, 2016 (CN) .................. 201610204380.X

(51) Int. Cl.
| | |
|---|---|
| A61K 39/12 | (2006.01) |
| A61K 31/337 | (2006.01) |
| A61K 31/44 | (2006.01) |
| A61K 31/7036 | (2006.01) |
| A61K 31/713 | (2006.01) |
| A61K 33/00 | (2006.01) |
| A61K 33/06 | (2006.01) |
| A61K 33/24 | (2019.01) |
| A61K 33/243 | (2019.01) |
| A61K 33/244 | (2019.01) |
| A61K 35/766 | (2015.01) |
| A61K 39/39 | (2006.01) |
| A61K 45/06 | (2006.01) |
| A61P 35/00 | (2006.01) |
| A61K 39/00 | (2006.01) |

(52) U.S. Cl.
CPC ............ *A61K 39/39* (2013.01); *A61K 31/337* (2013.01); *A61K 31/44* (2013.01); *A61K 31/7036* (2013.01); *A61K 31/713* (2013.01); *A61K 33/06* (2013.01); *A61K 33/24* (2013.01); *A61K 33/243* (2019.01); *A61K 33/244* (2019.01); *A61K 35/766* (2013.01); *A61K 39/12* (2013.01); *A61K 45/06* (2013.01); *A61P 35/00* (2018.01); A61K 2039/5252 (2013.01); A61K 2039/55561 (2013.01); A61K 2039/585 (2013.01); C12N 2760/20134 (2013.01); Y02A 50/30 (2018.01)

(58) Field of Classification Search
None
See application file for complete search history.

(56) References Cited

U.S. PATENT DOCUMENTS

2007/0160632 A1    7/2007  Haixiang

FOREIGN PATENT DOCUMENTS

| WO | 2006131023 | 12/2006 |
| WO | 2014052911 | 4/2014 |

OTHER PUBLICATIONS

Ammi et al., (2014) "Poly(I:C) as cancer vaccine adjuvant: Knocking on the door of medical breakthroughs", Pharmacology and Therapeutics, 146:120-131.
Desferal Novartis (2007) 9 pages: (https://www.accessdata.fda.gov/drugsatfda_docs/label/2007/016267s044lbl.pdf).
Ding (2014) "Oncolytic virus as a cancer stem cell killer: progress and challenges.", Stem Cell Investig, 1:22.
Forte et al., (2012) "Polyinosinic-Polycytidylic Acid Limits Tumor Outgrowth in a Mouse Model of Metastatic Lung Cancer", The Journal of Immunology, 188(11):5357-5364.
Glas et al., (2013) "Targeting the Cytosolic Innate Immune Receptors RIG-I and M DA5 Effectively Counteracts Cancer Cell Heterogeneity in Glioblastoma.", Stem Cells, 31:1064-1074.
Hirabayashi et al., (1999) "Inhibition of cancer cell growth by polyinosinic-polycytidylic acid/cationic liposome complex a new biological activity", Cancer Research, 59:4325-4333.
Philipov PV, (2009) "Adjuvant treatment of brain glioblastoma multiforme with rabies vaccine, deferoxamine and d-penicillamine: a pilot study.", J Biomed Clin Res., 2(1):49-53.
Starodubova et al., (2015) "Rabies Vaccines: Current Status and Prospects for Development.", Molecular Biology, 49(4):513-519.
Xinping et al., (2011) "Rapamycin enhances the activity of oncolytic herpes simplex virus against tumor cells that are resistant to virus replication", International Journal of Cancer, 129(6):1503-1510.
Xueqing et al., (2010) "Efficacy and safety/toxicity study of recombinant vaccinia virus JX-594 in two immunocompetent animal models of glioma.", Molecular Therapy, 18(11):1927-1936.
Zemp et al., (2013) "Treating brain tumor-initiating cells using a combination of myxoma virus and rapamycin", Neuro-Oncology, 15(7):904-920.

*Primary Examiner* — Nianxiang Zou
(74) *Attorney, Agent, or Firm* — Bozicevic, Field & Francis LLP; Shweta Chandra; Kyuoke Lim

(57) ABSTRACT

The present disclosure relates to a composition comprising PIC for treatment of cancer. More particularly, the present disclosure discloses a composition for treatment of cancer comprising polyinosinic-polycytidylic acid, an antibiotic or polyamine compound, a positive ion, and optionally a virus, and the use thereof in manufacture of a medicament for treatment of cancer. No figure for publication.

20 Claims, 15 Drawing Sheets

COMPOSITION COMPRISING PIC FOR TREATMENT OF CANCER

FIELD OF THE INVENTION

This application relates to medical field, especially treatment of cancer. More particularly, this application relates to a pharmaceutical composition for treatment of cancer comprising polyinosinic-polycytidylic acid (PIC), antibiotic or polyamine compound, positive ion, and optionally an inactivated or attenuated virus; and the use thereof for treatment of cancer.

BACKGROUND OF THE INVENTION

Cancer commonly refers to a malignant tumor. Under the influence of carcinogenic factors, some cells in tissues lose their normal growth regulation at the genetic level, leading to abnormal proliferation and differentiation, eventually becoming a tumor. Compared to a benign tumor, a malignant tumor grows faster, is invasive, prone to hemorrhagging, necrosis, ulceration, and often metastasis.

There are over 100 different known cancers that affect humans. The top 5 common sites of cancer are in the lung, prostate, colorectum, stomach, and liver cancer for men, and in the breast, colorectum, lung, cervix, and stomach cancer for women. Jie He and Wanqing Chen et al have published a paper named Cancer Statistics in China, 2015 in Cancer Journal for Clinicians. This research analysed and predicted the incidence and mortality rate of malignant tumor in China in the year of 2015. Data showed that China expected 4,292,000 new cases of malignant tumor in 2015. The five most common cancers are lung and bronchial cancer, stomach cancer, liver cancer, esophageal cancer and colorectal cancer for men, and breast cancer, lung cancer, stomach cancer, colorectal cancer and esophageal cancer for women. Lung cancer is one of the most common malignant tumors in China, being the highest malignant tumors mortality rate.

According to the World Health Organization (WHO), there are approximately 14 million new cancer cases and 8.2 million people die from cancer each year, which is an estimated 13% of all deaths worldwide. Cancer is the leading cause of death in both developed and developing countries. The burden is expected to grow worldwide with estimated new cancer cases rising by about 70% over the next two decades (WHO). Therefore, the increasing trend of cancer incidence has forced humankind to work more on the cancer prevention and treatments.

Currently the primary methods to treat cancer includes surgical treatment, chemotherapy which uses cancer cells killing drugs, radiation therapy which uses high energy radiation to kill cancer cells, targeted therapy which uses substances targeting specific cancer cells to deliver targeted therapy, and immunotherapy which uses immune system to treat cancer.

In addition, the application of virus in cancer treatment has gradually been noticed. In 1912, DePace discovered cervical tumor regression after inoculation of rabies vaccine to a female patient who was bitten by dog. Since then, there has been several reports on the use of virus for the treatment of cancer. Especially between 1950 to 1960, virus treatment of cancer underwent rapid development. In the 1970s, the development of virus treatment slowed down owing to the concern of virus pathogenicity, but the pace was picked up again in 1980s.

Guoqian Kuang et al described the potential mechanism of anticancer viruses, as well as the selection and method in clinical application (Current Status and Prospect of Cancer Virotherapy Clinical Studies, Journal of Guangxi Medical University, 1995 Vol. 12: 617-619). Currently, it is understood that the mechanism of anticancer viruses involves direct oncolytic action, enhancing immune system and stimulating release of cytokines. It is generally believed that the virus used in cancer treatment should be non-tumorigenic and with good antigenicity. Viruses reported for anticancer treatment includes: NDV, Mumps virus, Vaccinia virus, Sendai virus, HSV and Parvovirus (Kenney S et al., Viruses as oncolytic agents: a new age for "therapeutic" viruses. J Nati Cancer Inst, 1994, 86:1185). Lorence et al found in animal studies that live virus showed significantly better anti-cancer effect compared to inactivated virus (Complete regression of human neuroblastoma xenografts in athymic mice after local Newcastle disease virus therapy. J Nati Cancer Inst, 1994, 86:1228).

Some viruses can specifically kill tumor cells in cancer treatment, and are known as oncolytic virus. Oncolytic viruses can selectively replicate inside cancer cells, resulting in cytopathic effects and immune responses that leads to the death of tumor cells, while showing minimum effects on normal cells and tissues (Jiang Zhong, Oncolytic Virus and Tumor Treatment, Foreign Medicine (Microbiology Section), 2004 Vol. 27 Iss. No. 6).

At present, there is a significant number of reports on oncolytic viruses in the treatment of cancer. For example, WO2009/016433 describes using recombinant non-VSV rhabdovirus (such as Maraba virus, Carajas virus, Muir Springs virus, and/or Bahia grande virus) to cure hyperproliferative disease (e.g. cancer). US2010/0297072A1 discloses a composition for the treatment of cancer comprising oncolytic virus (paramyxovirus, reovirus, herpesvirus, adenovirus, and Semliki Forest virus) and an immunostimulant (CTLA-4 blocking agent, IL-21, anti-CD40 or granulocyte-macrophage colony stimulating factor (GM-CSF)), and administering this composition in MCA205 fibrosarcoma or B16 melanoma tumor-bearing mice significantly inhibited tumor growth.

Rabies virus belongs to the lyssavirus genus of rhabdoviridae family. Rabies virus has a distinct "bullet" shaped, helically symmetric nucleocapsid with an envelope, and contains single stranded RNA inside. Rabies virus is the pathogen for rabies disease. Anti-rabies immunization is one of the successful early vaccination examples. In the 1880s, Pasteur pioneered the use of vaccine. Early rabies vaccines were nerve tissue-derived, subsequently embryonated egg-cultured vaccines, cell culture vaccines, and subunit vaccines were developed. Genetically engineered vaccines are under development (Shounan Tan, Fengyu Zhang, Studies on Rabies and Human Rabies Vaccine. Medical Information 2011 Vol. 24:2841-2842). At present, the majority of rabies vaccines for human use are produced by inoculation of fixed virus strain (e.g., CTN-1V strain, aG strain) in Vero cells, culturing to obtain the virus in a liquid, followed by inactivation, concentration and purification, and further freeze-drying after adding appropriate an amount of gelatin or sucrose as a protective agent (Yuhui Zhang, The Establishment of Rabies Vaccine Purification Technology. Chinese Journal of Biologicals 1999 Vol. 12 Iss. No. 4: 231-232).

Jieguang Sun et al discovered that, by using rabies vaccine for human use as the sole active ingredient in the dosage of 2.5 IU to 10 IU daily through intramuscular injection route, the adverse effects of malignant tumor treatment were improved in an animal tumor model, and this also enhances macrophage phagocytosis (see CN100341571C). RU2414238C2 also reports a method of increasing cancer resistance, in which rabies vaccine increases the antitumor resistance of the organism to 9,10-dimethyl-1,2 benzanthracene.

Viruses have great potential in cancer treatment. Safer and more effective virus based anticancer drugs are needed in this field.

SUMMARY OF THE INVENTION

The present disclosure provides a composition for use in treatment of cancer, comprising or consisting of: a) polyinosinic-polycytidylic acid (PIC), b) at least one antibiotic or at least one polyamine compound, and c) at least one positive ion.

In another aspect, the present disclosure provides a composition for use in treatment of cancer, comprising or consisting of: a) polyriboinosinic—polyribocytidylic acid (PIC), b) at least one antibiotic or at least one polyamine compound, c) at least one positive ion, and d) optionally a virus.

In one embodiment, the composition comprises a) polyriboinosinic—polyribocytidylic acid (PIC), b) at least one antibiotic or at least one polyamine compound, c) at least one positive ion, and d) a virus.

In some embodiments, the virus is inactivated, attenuated, or incapable of replication in a human subject. In some particular embodiments, the virus is inactivated.

In some embodiments, the virus is selected from the group consisting of rhabdoviridae, adeniviridae, arena viridae, astroviridae, bunyaviridae, cliciviridae, flaviviridae, hepatitis delta virus, hepeviridae, mononegavirales, nidovirales, piconaviridae, orthomyxoviridae, papilloma viridae, parvoviridae, polyomaviridae, poxviridae, reoviridae, retroviridae, and togaviridae. In some particular embodiments, the virus belongs to Lyssavirus genus of rhabdoviridae family. In some particular embodiments, the virus is a rabies virus.

In some embodiments, the rabies virus is inactivated crude virus (e.g., hamster kidney cells inactivated crude rabies antigen (HKC-ICRA)), or inactivated purified virus (e.g., hamster kidney cell inactivated purified rabies antigen (HKC-IPRA)).

In some embodiments, the rabies virus suitable for use in the present disclosure is rabies vaccine including, but not limited to, inactivated, subunit, genetically modified, and polypeptide vaccine. In particular, the rabies virus vaccine suitable for use in the present disclosure is human diploid cell vaccine (HDCV), or hamster kidney cell inactivated purified rabies vaccine (HKC-IPRV), or hamster kidney cell inactivated crude rabies vaccine (HKC-ICRV), or purified Vero cell rabies vaccine (PVRV), or purified chicken embryo cell (PCEC) rabies vaccine, or purified duck embryo rabies vaccine (PDEV).

In some embodiments, the PIC are heterogeneous for molecular weight, where the molecular weight is equal to or greater than 66,000 Daltons. The value of 66,000 Daltons corresponds to the molecular size of 6.4 sedimentation unit (Svedbergs). In some embodiments, the molecular weight of PIC is from 66,000 to 1,200,000 Daltons (equivalent to 6.4 to 24.0 sedimentation unit). In some other embodiments, the molecular weight of PIC is equal to or greater than 150,000 Daltons. In some other embodiments, the molecular weight of PIC is from 100,000 to 200,000 Daltons, or from 300,000 to 4,000,000 Daltons, or from 500,000 to 1,000,000 Daltons, or from 1,000,000 to 1,500,000 Daltons, or from 1,500,000 to 2,000,000 Daltons, or from 2,000,000 to 2,500,000 Daltons, or from 2,500,000 to 3,000,000 Daltons, or from 3,000,000 to 3,500,000 Daltons, or from 3,500,000 to 4,000,000 Daltons, or from 4,000,000 to 4,500,000 Daltons, or from 4,500,000 to 5,000,000 Daltons.

In some particular embodiments, the antibiotic is selected from the group consisting of tacrolamycin, anthracycline, butyrin sulphate, gentamicin, hygromycin, amikacin, dideoxy kanamycin, nebramycin, β-lactam, neomycin, puromycin, streptomycin, streptozocin, and any combination thereof. The polyamine compound is selected from the group consisting of arginine salt, spermidine, N-(3-aminopropyl), N-(3-aminopropyl)-1,4-butanediamine, spermine, OS-dimethylaminothiophosphate, poly-lysine, aminoglycoside, and any combination thereof.

In some particular embodiments, the antibiotic is kanamycin. In some embodiments, the concentration of the antibiotic in the composition is from 10 unit/ml to 100,000 unit/ml, preferably from 100 unit/ml to 10,000 unit/ml, more preferably from 500 unit/ml to 5,000 unit/ml.

In some embodiments, the positive ion is a cation and is selected from the group consisting of calcium, cadmium, lithium, magnesium, cerium, cesium, chromium, cobalt, deuterium, gallium, iodine, iron, zinc, and any combination thereof. In some particular embodiments, the positive ion is calcium. The positive ion may be in the form of any suitable salt or organic complex including, but not limited to, chloride, fluoride, hydroxide, phosphate or sulfate. For example, when the positive ion is calcium, the calcium ion may be in the form of calcium carbonate, calcium chloride, calcium fluoride, calcium hydroxide, calcium phosphate or calcium sulfate. In some embodiments, the concentration of the positive ion in the composition is from 0.01 µmol to 10 mmol/ml, preferably from 0.02 µmol to 5 mmol/ml, more preferably from 0.1 µmol to 1 mmol/ml, most preferably from 0.1 µmol to 100 µmol/ml.

In some embodiments, the ratio of the virus to PIC is selected from the group consisting of: 1 IU/50 µg, 1 IU/60 µg, 1 IU/70 µg, 1 IU/80 µg, 1 IU/90 µg, 1 IU/100 µg, 1 IU/125 µg, 1 IU/200 µg, 1 IU/250 µg, 1 IU/300 µg, 1 IU/350 µg, 1 IU/400 µg, 1 IU/450 µg, 1 IU/500 µg, 1 IU/550 µg, 1 IU/600 µg, 1 IU/700 µg, 1 IU/800 µg, 1 IU/1000 µg, 1 IU/1500 µg, 1 IU/2000 µg, 1 IU/2500 µg, 1 IU/3000 µg, 1 IU/4000 µg, 1 IU/5000 µg, 1 IU6000 µg, 1 IU/7000 µg, 1 IU/8000 µg, 1 IU/9000 µg, 1 IU/10000 µg, and a range between any two of the above ratios. In particular, the ratio of said virus to said PIC is 1 IU/500 µg.

In some embodiments, the amount of PIC in the composition is from 250 µg to 5000 µg per unit dose; for example, the amount of the PIC is selected from the group consisting of 250 µg, 500 µg, 1000 µg, 1500 µg, 2000 µg, 3000 µg, 4000 µg, 5000 µg per unit dose and a range between any two of the above amounts.

In some particular embodiments, the amount of PIC in the composition is from 500 µg to 4000 µg per unit dose, or from 1000 µg to 3000 µg per unit dose, or from 1000 µg to 2500 µg per unit dose.

When the composition of the present disclosure is applied to adults, the amount of PIC in the composition is selected from the group consisting of 500 µg, 1000 µg, 1500 µg, 2000 µg per unit dose and a range between any two of the above amounts. When the composition of the present disclosure is applied to minors (e.g., children), the amount of PIC in the composition is selected from the group consisting of 250 µg, 500 µg, 1000 µg, 1250 µg per unit dose and a range between any two of the above amounts.

In some embodiments, the unit dose in the present disclosure is prepared into a volume which is selected from the group consisting of 0.1 ml, 0.15 ml, 0.2 ml, 0.5 ml, 1.0 ml, 1.5 ml, 2.0 ml, 2.5 ml, 3.0 ml, 4.0 ml, 5.0 ml, 10.0 ml, 20.0 ml, 30.0 ml, 40.0 ml, 50.0 ml, 60.0 ml, 70.0 ml, 80.0 ml, 90.0 ml, 100.0 ml, 150.0 ml, 200.0 ml, 250.0 ml, and a range between any two of the above volumes. It will be understood by the person skilled in the art that an administration volume that is too large or too small leads to inconvenience in clinical practice. Therefore, when the compositions of the present disclosure are administered to a human subject, the unit dose is preferably in the range of 0.5 ml to 1.0 ml for injection, preferably in the range of 0.15 ml to 0.2 ml for intranasal administration, preferably in the range of 30.0 ml to 100.0 ml for intravenous injection. It is understood that although the unit dose is expressed in volume, this does not mean that the composition of the present disclosure can only be in a liquid dosage form. When the composition of the present disclosure is prepared in a solid dosage form (dry or lyophilized powder), the volume per unit dose refers to the solution volume after reconstitution of the dry or lyophilized powder.

In some embodiments, the amount of the virus in the composition is from 0.1 IU to 100.0 IU per unit dose or from 0.2 to 100.0 IU per unit dose. In particular, the amount of the virus in the composition is selected from the group consisting of 0.2 IU, 0.5 IU, 1.0 IU, 1.5 IU, 2.0 IU, 2.5 IU, 3.0 IU, 3.5 IU, 4.0 IU, 5.0 IU, 6.0 IU, 7.0 IU, 8.0 IU, 9.0 IU, 10.0 IU, 15.0 IU, 20.0 IU, 30.0 IU, 40.0 IU, 50.0 IU, 60.0 IU, 70.0 IU, 80.0 IU, 90.0 IU, 100.0 IU per unit dose, and a range between any two of the above amounts. In some particular embodiments, the amount of the virus in the composition is from 0.5 IU to 3.0 IU per unit dose; preferably from 1.0 IU to 2.5 IU per unit dose. In some particular embodiments, when applied to adults, the amount of the virus in the composition is from 0.5 IU to 10.0 IU per unit dose. In some other particular embodiments, when applied to minors, the amount of the virus in the composition is from 0.5 IU to 5.0 IU per unit dose.

In some embodiments, the concentration of the virus in the composition is from 0.05 IU/ml to 40.0 IU/ml; preferably selected from the group consisting of 0.05 IU/ml, 0.1 IU/ml, 0.15 IU/ml, 0.2 IU/ml, 0.5 IU/ml, 1.0 IU/ml, 2.0 IU/ml, 3.0 IU/ml, 4.0 IU/ml, 5.0 IU/ml, 10 IU/ml, 15 IU/ml, 20 IU/ml, 25 IU/ml, 30 IU/ml, 35 IU/ml, 40 IU/ml.

In some embodiments, the composition of present disclosure further comprises at least one auxiliary material as excipient and stabilizer. The auxiliary material is selected from the group consisting of gelatin, sucrose, sugar, lactose, maltose, trehalose, glucose, low molecular weight dextran, sorbitol, polysorbate 20, mannitol polyethylene glycol, human serum albumin, recombinant albumin, sodium octoate, urea, aluminum hydroxide, phenol red, magnesium chloride, potassium chloride, sodium chloride, sodium thiosulfate, potassium dihydrogen phosphate, ascorbic acid, trichloromethane, phenol, and thimerosal and any combination thereof.

In some embodiments, the composition of present disclosure further comprises at least one physiologically acceptable buffer which is selected from the group consisting of acetate, tris(hydroxymethyl)aminomethane (tris), bicarbonate, carbonate, phosphate buffer and any combination thereof. The pH of the buffer or composition is selected from the group consisting of 6.50, 6.60, 6.70, 6.80, 6.90, 7.00, 7.05, 7.10, 7.15, 7.20, 7.25, 7.30, 7.35, 7.40, 7.45, 7.50, 7.55, 7.60, 7.65, 7.70, 7.75, 7.80, 7.85, 7.90, 7.95, 8.00, and a range between any two of the above pH values. In one embodiment, the pH of the composition is between pH 6.5 to pH 8.0. In some particular embodiments, the buffer is PBS, and the pH of the buffer or composition is from 7.3 to 7.5.

The composition of the present disclosure may be prepared in a solid dosage form or a liquid dosage form. The composition of present disclosure may be prepared in the form selected from the group consisting of a dry powder, a liquid solution or a liquid dosage form (e.g., injectable solution, aqueous or physiological saline solution, suspension, ointment, droplet, emulsion, gel, syrup or serofluid), tablet, coated tablet, microcapsule, suppository, granule, sugar-coated tablet, capsule. The method of preparation is generally described in Vaccine 4th Edition (Stanley A Plotkin et al., W. B. Saunders Company 2003). Preferably, the composition of present disclosure is prepared in the form of an injectable solution.

In another aspect, the present disclosure provides a composition for use in treatment of cancer, which is in the form of a dry powder or lyophilized powder.

In another aspect, the present disclosure provides the use of the combination of PIC, at least one antibiotic (or at least one polyamine compound) and at least one positive ion in the manufacture of a medicament for treatment of cancer.

In another aspect, the present disclosure provides the use of the combination comprising a PIC adjuvant disclosed in CN103405762A in the manufacture of a medicament for treatment of cancer.

In another aspect, the present disclosure provides the use of the combination of PIC, at least one antibiotic (or, at least one polyamine compound), at least one positive ion and a virus in the manufacture of a medicament for treatment of cancer.

In another aspect, the present disclosure provides the use of the composition for treatment of cancer.

More particularly, the present disclosure provides the use of the composition in the manufacture of a medicament for treatment of cancer.

In some particular embodiments, the cancer is selected from the group consisting of:
 oropharyngeal cancer, nasopharyngeal carcinoma, esophageal cancer, gastric cancer, colon cancer, liver cancer, cholangiocarcinoma, gallbladder cancer, pancreatic cancer, lung cancer, tracheal cancer, thymoma, bone cancer, joint cancer, melanoma, mesothelial cancer, breast cancer, cervical cancer, ovarian cancer, prostate cancer, brain cancer, myleloma, blood cancer;
 lip malignant neoplasm, tongue root malignant neoplasm, gingival malignant neoplasm, mouth malignant neoplasm, palate malignant neoplasm, parotid malignant neoplasm, tonsil malignant neoplasm, oropharyngeal malignant neoplasm, nasopharyngeal malignant neoplasm, piriform sinus malignant neoplasm, hypopharynx malignant neoplasm;
 esophagus malignant neoplasm, gastric malignant neoplasm, small intestine malignant neoplasm, colon malignant neoplasm, rectosigmoid junction malignant neoplasm, rectal malignant neoplasm, anal and anal canal malignant neoplasm, liver and intrahepatic bile duct malignant neoplasm, gallbladder malignant neoplasm, pancreatic malignant neoplasm;
 nasal and middle ear malignant neoplasm, nasal sinus malignant neoplasm, laryngeal malignant neoplasm, tracheal malignant neoplasm, bronchial and pulmonary malignant neoplasm, thymus malignant neoplasm, heart, mediastinal and pleural malignant neoplasm;
 bone and articular cartilage malignant neoplasm;
 skin malignant melanoma;
 mesothelial and soft tissue malignant neoplasm;
 breast malignant neoplasm;

genital malignant neoplasm, vaginal malignant neoplasm, cervical malignant neoplasm, uterine malignant neoplasm, ovarian malignant neoplasm, placental malignant neoplasm;

penile malignant neoplasm, prostate malignant neoplasm, testicular malignant neoplasm;

urinary tract malignant neoplasm;

eye and appendage malignant neoplasm;

meningeal malignant neoplasm, brain malignant neoplasm;

spinal cord, cranial nerve and central nervous system malignant neoplasm;

endocrine gland malignant neoplasm;

Hodgkin's disease, follicular nodular non-Hodgkin's lymphoma, diffuse non-Hodgkin's lymphoma, peripheral and cutaneous T-cell lymphoma, multiple myeloma, malignant plasma cell tumor, lymphoid leukemia, myeloid leukemia, monocytic leukemia.

In some particular preferable embodiments, the composition of present disclosure is used in treatment of cancer which is selected from the group consisting of lung cancer, breast cancer, thyroid cancer, kidney cancer, gastric adenocarcinoma, liver cancer, melanoma, tongue cancer, rectal cancer, endometrial cancer, and ovarian cancer.

In a further preferable embodiment, the composition of present disclosure is used in treatment of metastatic tumor.

In further embodiments, the present disclosure provides the use of the composition in combination with an anti-tumor treatment regimen in the manufacture of a medicament for treatment of cancer;

preferably, said anti-tumor treatment regimen is selected from the group consisting of chemotherapy, radiotherapy, targeted therapy, and immunotherapy, wherein therapeutical agent used in said chemotherapy is selected from the group consisting of alkylating agent, anti-metabolic antineoplastic agent, anti-tumor antibiotic, anti-tumor botanical, platinum compound antineoplastic agent, hormonal balance antineoplastic agent, and miscellaneous antineoplastic agent, wherein therapeutical agent used in said targeted therapy is selected from the group consisting of rituximab, bevacizumab, trastuzumab, imatinib, dinoxetine, cetuximab, nilotinib, and sorafenib, wherein therapeutical agent used in said immunotherapy is selected from the group consisting of PD-1 inhibitor, PD-L1 inhibitor and CTLA4 inhibitor; more preferably, said alkylating agent is selected from the group consisting of cyclophosphamide, ifosfamide and thiotepa, said anti-metabolic antineoplastic agent is selected from the group consisting of methotrexate, mercaptopurine, fluorouracil and cytarabine, said anti-tumor antibiotic is selected from the group consisting of bleomycin, daunorubicin, actinomycin D, mitomycin, doxorubicin and mitoxantrone, said anti-tumor botanical is selected from the group consisting of vincristine, etoposide, teniposide, paclitaxel and docetaxel, said platinum compound antineoplastic agent is selected from the group consisting of cisplatin, carboplatin and oxaliplatin, said hormone balance antineoplastic agent is selected from the group consisting of leuprolide, tamoxifen, flutamide and formestane, said miscellaneous antineoplastic agent is arsenic trioxide.

Alternatively, the present invention includes the use of a composition disclosed herein in the manufacture of a medicament for treatment of cancer; wherein the medicament is for use in combination with an anti-tumour treatment regimen. Preferably, said anti-tumor treatment regimen is selected from the group consisting of chemotherapy, radiotherapy, targeted therapy, and immunotherapy, wherein therapeutical agent used in said chemotherapy is selected from the group consisting of alkylating agent, anti-metabolic antineoplastic agent, anti-tumor antibiotic, anti-tumor botanical, platinum compound antineoplastic agent, hormonal balance antineoplastic agent, and miscellaneous antineoplastic agent, wherein therapeutical agent used in said targeted therapy is selected from the group consisting of rituximab, bevacizumab, trastuzumab, imatinib, dinoxetine, cetuximab, nilotinib, and sorafenib, wherein therapeutical agent used in said immunotherapy is selected from the group consisting of PD-1 inhibitor, PD-L1 inhibitor and CTLA4 inhibitor; more preferably, said alkylating agent is selected from the group consisting of cyclophosphamide, ifosfamide and thiotepa, said anti-metabolic antineoplastic agent is selected from the group consisting of methotrexate, mercaptopurine, fluorouracil and cytarabine, said anti-tumor antibiotic is selected from the group consisting of bleomycin, daunorubicin, actinomycin D, mitomycin, doxorubicin and mitoxantrone, said anti-tumor botanical is selected from the group consisting of vincristine, etoposide, teniposide, paclitaxel and docetaxel, said platinum compound antineoplastic agent is selected from the group consisting of cisplatin, carboplatin and oxaliplatin, said hormone balance antineoplastic agent is selected from the group consisting of leuprolide, tamoxifen, flutamide and formestane, said miscellaneous antineoplastic agent is arsenic trioxide.

The present invention also includes use of a composition disclosed herein the manufacture of a medicament for treatment of cancer and use of at least one further anti-tumour agent in the manufacture of a medicament for treatment of cancer. The present invention also includes use of a composition disclosed herein and at least one further anti-tumour agent in the manufacture of a medicament for treatment of cancer.

Preferably, the anti-tumour compound is selected from the group consisting of a chemotherapeutic agent, a targeted therapeutic agent and an immunotherapeutic agent.

Preferably, the chemotherapeutic agent is selected from the group consisting of alkylating agent, anti-metabolic antineoplastic agent, anti-tumor antibiotic, anti-tumor botanical, platinum compound antineoplastic agent, hormonal balance antineoplastic agent, and miscellaneous antineoplastic agent.

Preferably, said targeted therapeutical agent is selected from the group consisting of rituximab, bevacizumab, trastuzumab, imatinib, dinoxetine, cetuximab, nilotinib, and sorafenib.

Preferably, said immunotherapeutical agent is selected from the group consisting of PD-1 inhibitor, PD-L1 inhibitor and CTLA4 inhibitor;

Preferably, said alkylating agent is selected from the group consisting of cyclophosphamide, ifosfamide and thiotepa.

Preferably, said anti-metabolic antineoplastic agent is selected from the group consisting of methotrexate, mercaptopurine, fluorouracil and cytarabine.

Preferably, said anti-tumor antibiotic is selected from the group consisting of bleomycin, daunorubicin, actinomycin D, mitomycin, doxorubicin and mitoxantrone.

Preferably, said anti-tumor botanical is selected from the group consisting of vincristine, etoposide, teniposide, paclitaxel and docetaxel, Preferably, said platinum compound antineoplastic agent is selected from the group consisting of cisplatin, carboplatin and oxaliplatin.

Preferably, said hormone balance antineoplastic agent is selected from the group consisting of leuprolide, tamoxifen, flutamide and formestane Preferably, said miscellaneous antineoplastic agent is arsenic trioxide.

In the context of present disclosure, when the composition of present disclosure comprises a virus, the cancer to be treated is not caused by the virus in the composition. In some particular embodiments, the cancer to be treated is not caused by rabies virus.

In another aspect, the present disclosure provides a method for treatment of cancer, comprising a step of administering a therapeutically effective amount of the composition to a subject, for example a human subject.

In some embodiments, the administration of the composition is systemic or localized. In some embodiments, the composition is administered via parenteral injection (e.g., intramuscular, intraperitoneal, intravenous, subcutaneous, intradermal, intratumoral, peritumoral). In some other embodiments, the composition is intradermally administered via a route other than injection (e.g., a route that does not destroy the epithelial cell barrier by mechanical means). In some other embodiments, the composition is administered via a rectal, vaginal, nasal (for example intranasal), oral, buccal, sublingual, respiratory, ocular (for example intraocular), or transdermal route.

In particular, examples of the administration route include intramuscular, intraperitoneal, intravenous, subcutaneous, transdermal, intradermal, intranasal, intraocular, oral, sublingual, intratumoral, and peritumoral.

In some embodiments, the composition of present disclosure is administered to a human subject based on the frequency selected from the group consisting of once per month, 2 times per month, 3 times per month, 4 times per month, 5 times per month, 6 times per month, 7 times per month, 8 times per month, once per week, 2 times per week, 3 times per week, 4 times per week, 5 times per week, 6 times per week, once every three days, 2 times every three days, 3 times every three days, once every two days, 2 times every two days, once per day, 2 times per day.

In particular, the method comprises administering a therapeutically effective amount of a composition according to the invention to a human subject through intramuscular injection at a frequency of 2 times every three days, or administering a therapeutically effective amount of the composition according to the invention to a human subject through intramuscular injection at a frequency of once per week.

In another aspect, the present disclosure provides a pharmaceutical kit or a kit for use in implementating said treatment method comprising at least one container, wherein each of said container independently comprises the composition of present disclosure. The composition and/or amount of the composition in the different containers may be the same or different.

In some embodiments, the kit of the present disclosure comprises at least one container containing 2.0 IU/ml of inactivated rabies virus and 1000 μg/ml of PIC.

In some embodiments, the composition of present disclosure is formulated in sterile liquid and is contained in sterile container (e.g., tube, bottle, ampoule, syringe). In other embodiments, the composition of present disclosure is contained in a container in the form of dry or lyophilized powder which is reconstituted into liquid form before use.

In some embodiments, the kit of present disclosure further comprises the item selected from the group consisting of needle, water for injection, instruction for use, and any combination thereof.

Definitions

As used herein, the term "comprising" or "including" is to be interpreted as specifying the presence of the stated features, integers, steps or components as referred to, but does not preclude the presence or addition of one or more features, integers, steps or components, or groups thereof. However, in context with the present disclosure, the term "comprising" or "including" also includes "consisting of". The variations of the word "comprising", such as "comprise" and "comprises", and "including", such as "include" and "includes", have correspondingly varied meanings.

"Inactivated" refers to the removal of virus pathogenicity and/or reprlicative capacity, but maintaining the ability to induce a protective immune response in human body. Virus inactivation strategies are known in the industry. Any common method can be used to inactivate the virus, and a suitable method may be selected for a specific virus type. Virus inactivation methods including but not limited to: using a photoreactive compound, an oxidizing agent, radiation (e.g., UV radiation, γ-radiation), UV radiation in combination with riboflavin, solvent/detergent (S/D) treatment (such as using tri(nbutyl)phosphate and/or Tween 80), polyethylene glycol (PEG) treatment, pasteurization (heat treatment), acidic pH treatment, enzyme treatment (pepsin or trypsin), methylene blue light treatment, with dimethyl methylene blue and visible light, psoralen derivative S-59 and UVA irradiation treatment.

"Attenuated", An attenuated virus is still viable but the virulence is reduced during the manufacturing process. Attenuated virus retains the ability to replicate and stimulate the human body to induce immune response.

The term "heterogeneous" as used herein in the context of the composition of present disclosure indicates that the PIC molecules in the composition are not uniform with respect to molecular weight, size, or both.

The term "unit dose" as used herein refers to physically discrete units suitable as unitary dosages for human subjects. Each unit contains a predetermined amount of present composition sufficient to produce the desired effect in combination with the pharmaceutically/physiologically acceptable diluent or carrier.

The term "treatment", "treating", "treat" and the like are used herein to generally refer to obtaining a desired pharmacological and/or physiological effect. The effect may be prophylactic in terms of completely or partially preventing a disease or symptom thereof and/or may be therapeutic in terms of a partial or complete stabilization or cure of a disease and/or adverse effect attributable to the disease. "Treatment" as used herein covers any treatment of a disease in subject, particularly a human, and includes: (i) preventing the disease from occurring in a subject which may be predisposed to the disease but has not yet been diagnosed as having it; (ii) inhibiting the disease, i.e., arresting its development; or (iii) relieving the disease, i.e., causing regression of the disease.

In the present disclosure, when describing numerical range, the expression " . . . to . . . ", "within the range", "arrange between" and the like include the endpoint values.

As used herein, the term virus refers to a whole virus or a fragment of a virus and includes a virus vaccine as well as a viral antigen.

The following examples and drawings and descriptions of the drawings are only for the purpose of specifically illustrating the present invention, and is not intended to limit the scope of the invention.

BRIEF DESCRIPTION OF THE DRAWINGS

FIG. 24A shows the CT scan before administration of YS-ON-001; FIG. 24B shows the CT scan after two courses of YS-ON-001 treatment.

EXAMPLES

Having now generally described the invention, the same will be more readily understood through reference to the following examples which are provided by way of illustration, and are not intended to be limiting of the present invention.

Unless otherwise stated, the animal studies described in this disclosure were conducted in accordance with Regulations on the Administration of Laboratory Animals, Guidance on the Care of Laboratory Animals, and China National Standard GB/14925.

Example 1. The Manufacture Method of the Composition of Present Disclosure

1. Virus:
Inactivated rabies virus.
2. The composition of present disclosure is prepared according to the following components:
The composition comprises inactivated rabies virus, PIC, Kanamycin and calcium chloride. The composition further comprises auxiliary materials including maltose, dextran and human serum albumin.

Wherein, inactivated rabies virus: PIC=2.0 IU: 1000 μg.

Under sterile condition, the above composition is formulated in a physiologically acceptable buffer. The concentration and volume of the composition to be formulated are allowed to be adjusted according to the factors including subject to be administered (including but not limited to age, sex, body weight, health condition), cancer condition (including but not limited to cancer type, severity), administration route, and administration frequency. For the same therapeutically effective amount, when the concentration of the composition is high, the administration volume is small; when the concentration of the composition is low, the administration volume is large.

When the composition is applied to mouse, the composition YS-ON-001 is prepared in the concentration of 2.0 IU/mL inactivated rabies virus, 1000 μg/mL PIC, 800 IU/mL kanamycin and 0.16 μmol/mL calcium ion.

Figure 1:
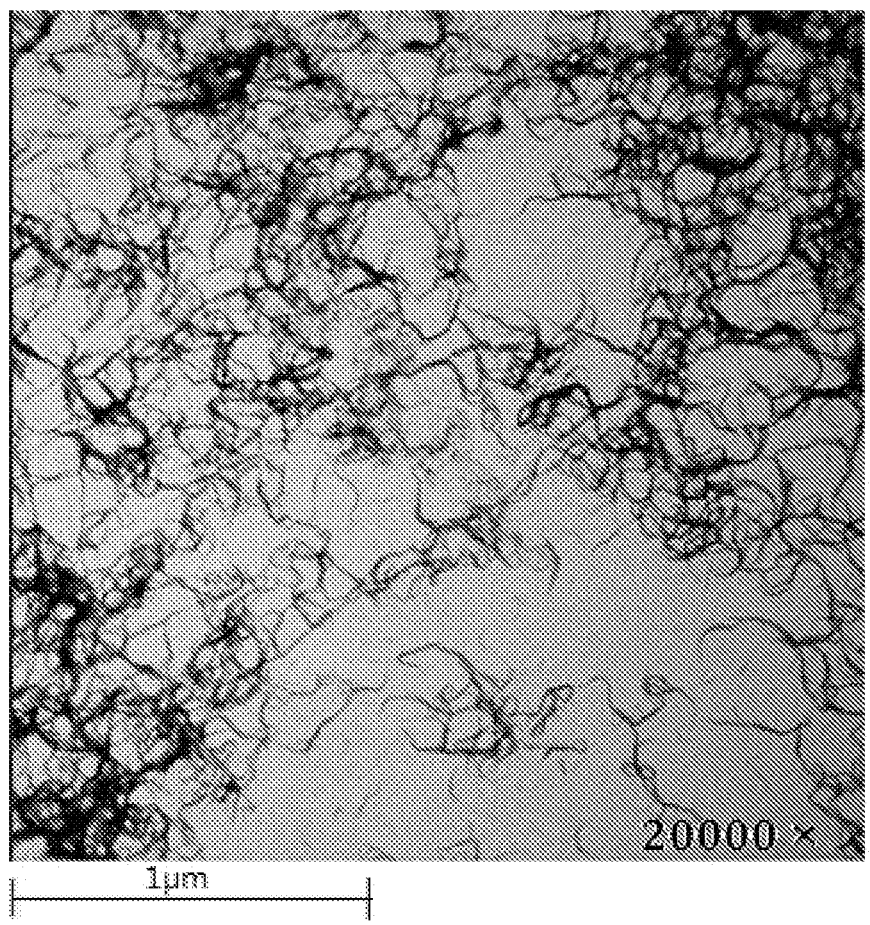
FIG. 1. The structure of PIC, antibiotic (or polyamine compound) and positive ion observed under electron microscopy.

PIC is unstable in human body, and can be quickly broken down by nuclease. Antibiotic (or polyamine compound) and positive ion can form a three-dimensional structure with PIC, thereby increasing PIC stability. Electron microscope shows the final structure in FIG. 1.

Example 2. Therapeutic Effects of the Composition (YS-ON-001) in Lung Cancer Animal Model I. Construction of tumor model
1. Animals
1.1 Female C57BL/6 mice (6 weeks old, body weight 17.5±0.1 g) were obtained from Shanghai SIPPR-BK Laboratory Animal Co. Ltd.
1.2 Animal Husbandry
Animals were fed according to the SPF level animal feeding conditions, and were provided with food (Keaoxieli certified Rodent Diet). Cage, bedding, feed and drinking water were autoclaved. Cages were placed in the laminar flow rack with the cleanliness of 100, 3-5 animals per cage, and cages were replaced twice a week. The temperature in animal room is 21 to 25° C., with the relative humidity between 40% and 70%.
2. Tumor Cell Line
The murine Lewis lung cancer cell line LL/2 (ATCC® CRL-1642™) was obtained from American Type Culture Collection (ATCC). Cells were maintained in DMEM with 10% fetal bovine serum in a atmosphere of 5% $CO_2$ at 37° C. Passaging ratio was between 1:5 and 1:8, at the frequency of 3 to 4 times per week.
3. Construction of LL/2 Tumor Transplanting Model
LL/2 murine Lewis lung tumor model was established in female C57BL/6 mice by subcutaneous inoculation with $1 \times 10^6$ cells per animal. The rate of tumor formation was 100%. Three days post cell inoculation, the cell inoculated mice were randomly sorted into treatment groups by weight. Animals in each group were administered according to Table 1.

II. Test Method
1. Test Groups
There were 4 groups: Vehicle group, Cisplatin group, YS-ON-001 low dose group, and YS-ON-001 high dose group.

TABLE 1

Experimental Design for LL/2

| Group | Treatment | N | Route of Administration | Dosing Level | Schedule |
|---|---|---|---|---|---|
| 1 | Vehicle (negative control) | 10 | i.m | 0.2 mL/mouse | q3d, total 6 dosing |
| 2 | Cisplatin (positive control) | 10 | i.v | 5 mg/kg | QW, total 3 dosing |
| 3 | The composition YS-ON-001 | 10 | i.m | 0.1 mL/mouse | q3d, total 6 dosing |
| 4 | The composition YS-ON-001 | 10 | i.m | 0.2 mL/mouse | q3d, total 6 dosing |

Group 1: In vehicle group, DPBS was injected into both hind legs at 0.1 mL/site.
Group 3: YS-ON-001 low dose group, 0.1 mL of YS-ON-001 was injected into right hind leg and 0.1 mL of DPBS was injected into left hind leg in 0,1 mL/mouse
Group 4: YS-ON-001 high dose group, YS-ON-001 was injected into both hind legs at 0.1 mL/site, in total 0.2 mL.

2. The Studies were Terminated when the Average Tumor Volume in Vehicle Group Reached 2500 $mm^3$
3. At the end of study, the tumor mass was removed and photographed. The tumor weight was recorded. The thymus and spleen was removed and weighed. And then, the organ index was calculated.

Figure 2A:
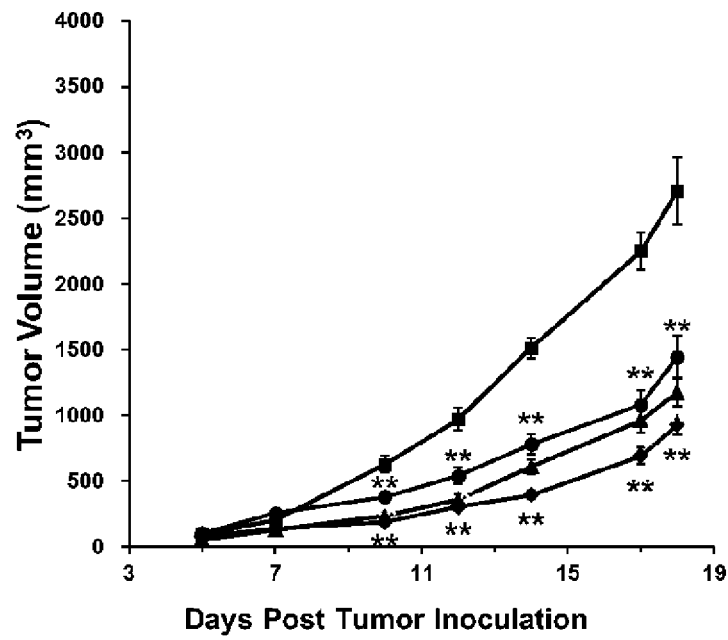
FIG. 2A. Tumor volume of LL/2 tumor-bearing mice after treatment. ■Vehicle control group, •Cisplatin group, ΔYS-ON-001 low dose group, ◇YS-ON-001 high dose group. Bar represented SEM. **: p<0.01 vs. vehicle control group.
Figure 2B:
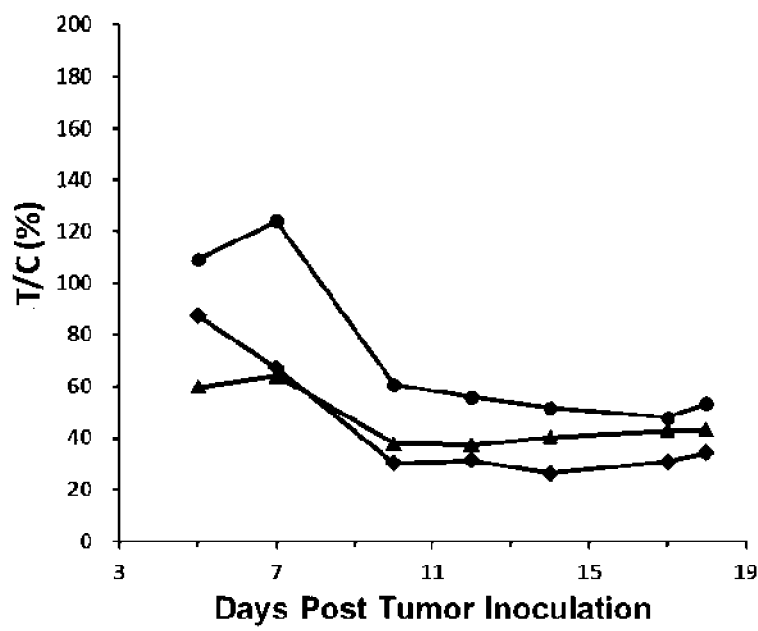
FIG. 2B. Relative tumor proliferation rate (T/C) of LL/2 tumor-bearing mice after treatment. •Cisplatin group, ΔYS-ON-001 low dose group, ◇YS-ON-001 high dose group.
Figure 3:
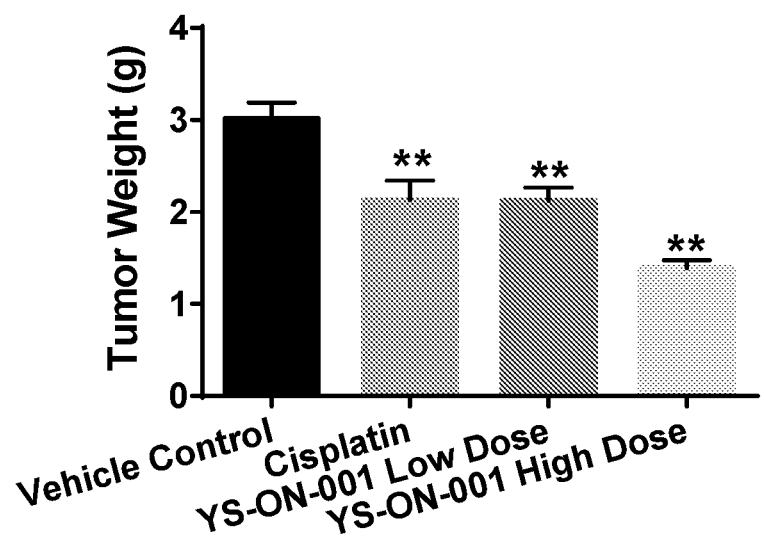
FIG. 3. Tumor weight of LL/2 tumor-bearing mice after treatment. **: p<0.01 vs. vehicle control group. #: p<0.05 vs. YS-ON-001 high dose group.

III. Observational Indices
1. Tumor Volume
The anti-tumor effect of the test article was observed by measuring tumor diameter. Tumor volumes were measured 3 times weekly and the relative tumor proliferation rate T/C (%) was calculated.
1.1 Tumor volume (TV) was calculated as follow:

$$TV = \frac{1}{2} \times a \times b^2$$

where a and b denote long and wide, respectively.
1.2 Relative Tumor Proliferation Rate T/C (%)=$TV_t/TV_c \times$ 100%
Where $TV_t$ is the mean tumor volume of the treatment group and $TV_c$ is the mean tumor volume of the vehicle control group.
2. Tumor Weight
At the end of study, tumor mass was removed and weighed. Record the tumor weight and calculate the tumor inhibition rate according to the following formula:

$$\text{Tumor inhibition rate} = (TW_C - TW_T)/TW_C \times 100\%$$

Where $TW_t$ is the mean tumor weight of the treatment group and $TV_c$ is the mean tumor weight of the vehicle control group.
3 Body Weight
Body weight of each mouse was weighed three times a week. Body weight change (BWC) was calculated as:

$$BWC = (BW_n - BW_0)/BW_0 \times 100\%$$

Where $BW_n$ is the BW at Day n and $BW_0$ is the BW at the day when the treatment was initiated.
4 Thymus and Spleen Weight
At the end of study, thymus and spleen was removed and weighed. Organ index was calculated as: organ index=organ weight/body weight×100%.
IV. Data Presentation and Analysis
Data were reported as Mean±SEM. Comparison between groups was analysed using ANOVA.
V. Results
1. Tumor Volume
A graphical presentation of the effect of YS-ON-001 on LL/2 murine Lewis lung tumor volume is shown in FIG. 2A.
A graphical presentation of the effect of YS-ON-001 on LL/2 murine Lewis lung tumor proliferation rate is shown in FIG. 2B.
Take the day of the tumor as Day 0. On Day 3, animals were randomized by body weight and administered according to group assignment.
Tumors in the vehicle control group grew progressively in all ten mice. At the end of study, the mean tumor volume reached 2707±257 $mm^3$.
Treatment with Cisplatin significantly inhibited the tumor growth starting from Day 10 till end of the study, resulting in a relative tumor proliferation rate of 53.04%, with a significant difference compared to the vehicle control group. ($p<0.01$).
YS-ON-001 treatment significantly inhibit tumor growth starting from Day 10 till end of the study compared to vehicle control group ($p<0.01$). The tumor volume in high dose group is lower than that in low dose group, however the difference is not significant ($p>0.05$). The relative tumor proliferation rate at the end of the study is 43.36% and 34.33%, respectively.
2. Tumor Weight
A graphical presentation of the effect of YS-ON-001 on LL/2 murine Lewis lung tumor weight is shown in FIG. 3.

At the end of study, the tumor mass was removed and weighed. Similar with tumor volume, Treatment with Cisplatin or YS-ON-001 significantly lower the tumor weight compared to the vehicle control group (p<0.01). The tumor weight in YS-ON-001 high dose group is significantly lower than that in Cisplatin group and YS-ON-001 low dose group (p<0.05). The inhibition rate is 29.46%, 29.49% and 53.87%, for Cisplatin group, YS-ON-001 low dose and high dose group, respectively.

3. Body Weight

Figure 4:
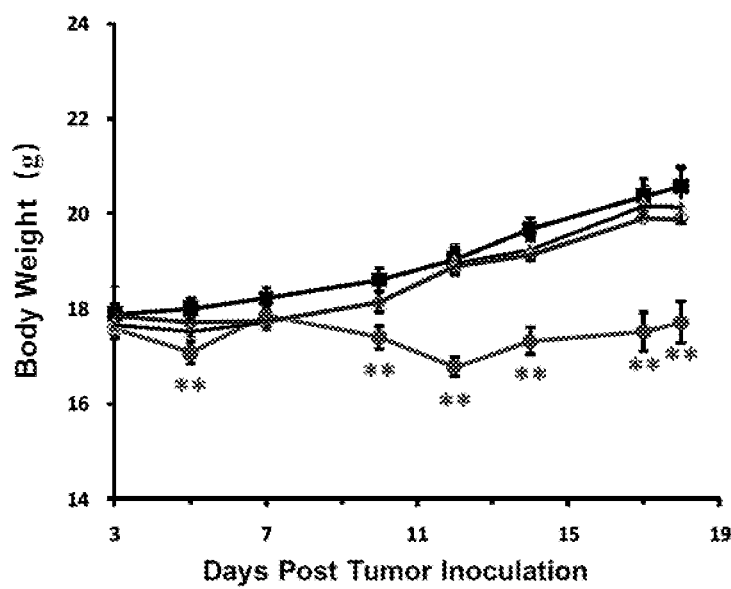
FIG. 4. Body weight of LL/2 tumor-bearing mice after treatment. ■Vehicle control group, •Cisplatin group, ΔYS-ON-001 low dose group, ◇YS-ON-001 high dose group. Bar represented SEM. **: p<0.01 vs. vehicle control group.
Figure 5:
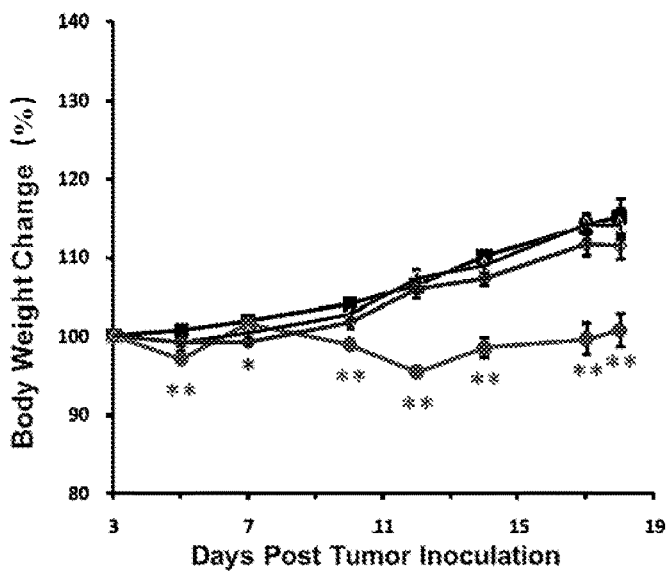
FIG. 5. Body weight change of LL/2 tumor-bearing mice after treatment. ■Vehicle control group, •Cisplatin group, ΔYS-ON-001 low dose group, ◇YS-ON-001 high dose group. Bar represented SEM. *: p<0.05 vs. vehicle control group. **: p<0.01 vs. vehicle control group.

A graphical presentation of the effect of YS-ON-001 on body weight and body weight changes of LL/2 murine Lewis lung tumor is shown in FIGS. 4 & 5.

The average body weight (BW) was significantly affected by the treatment of Cisplatin compared to the vehicle group on Day 5 and from Day 10 to end of study (p<0.01). The same result was observed on the body weight change.

The mouse body weight was not obviously effected by the treatment of two YS-ON-001 groups compared to vehicle group (p>0.05). The body weight change in YS-ON-001 high dose group was significantly lower on Day 7 compared to vehicle control group (p<0.05), while there was no significant change at other time points.

4. Thymus and Spleen Weight

Figure 6A:
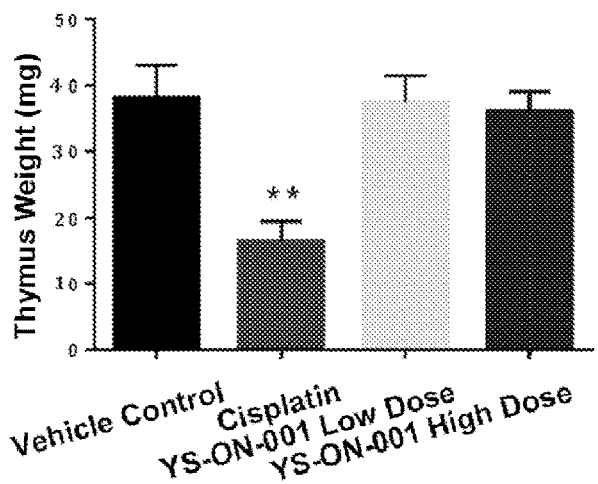
FIGS. 6A & 6B. Thymus weight and thymus index of LL/2 tumor-bearing mice after treatment. **: p<0.01 vs. vehicle control group.
Figure 6B:
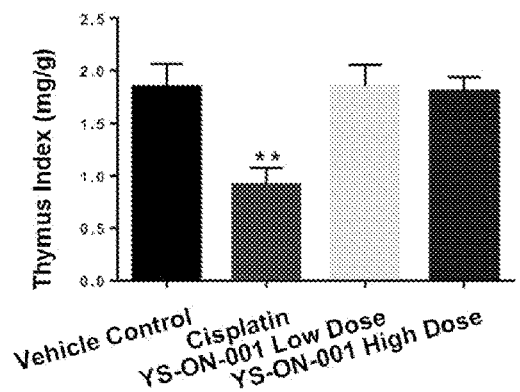
Figure 7A:
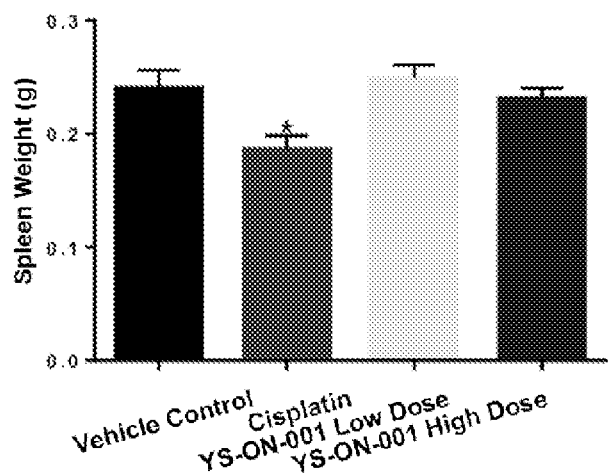
FIGS. 7A & 7B. Spleen weight and spleen index of LL/2 tumor-bearing mice after treatment. *: p<0.05 vs. vehicle control group.
Figure 7B:
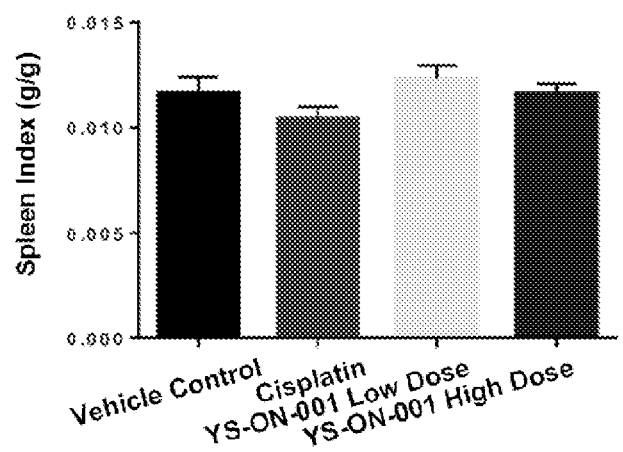

A graphical presentation of the thymus and spleen weight as well as organ index of LL/2 murine Lewis lung tumor is shown in FIGS. 6 & 7.

At the end of study, except tumor mass, the thymus and spleen was removed and weighed. Compared to the vehicle group, Cisplatin treatment significantly reduced thymus weight and spleen weight. The thymus weight and thymus index is significantly reduced compared to that in vehicle control group (p<0.01). The spleen weight is significantly reduced compared to that in vehicle control group (p<0.05), however the spleen index shows a trend of reducing which is not significant (p>0.05). The thymus weight, spleen weight and their organ index were not affected by the treatment of YS-ON-001 compared to the vehicle group.

VI. Discussion and Conclusion

In the present example, the vehicle control group had a strong tumor growth and the cisplatin group showed a significant inhibitory effect on tumor growth as a positive control.

YS-ON-001 showed anti-tumor activity in a dose-dependent manner when used as a single agent at 0.1 mL/mouse and 0.2 mL/mouse.

Moreover, the animals were well tolerated and showed no significant effect on body weight, spleen weight and thymus weight. The side effects were significantly lower than those in Cisplatin group. The antitumor effect in YS-ON-001 high dose group was better than that in Cisplatin group.

The results showed that YS-ON-001 showed inhibitory effect in a dose-dependent manner on tumor growth at the tested dose level in LL/2 Lewis lung cancer animal model. Meanwhile the tumor-bearing mice showed no obvious side effects.

Example 3. Therapeutic Effects of the Composition (YS-ON-001) in Breast Cancer Animal Model I. Construction of Tumor Model
1. Animals
1.1 Female Balb/c mice (6 weeks old, body weight 17.2±0.1 g) were obtained from Shanghai SIPPR-BK Laboratory Animal Co. Ltd.

2.2. Animal Husbandry

Animals were fed according to the SPF level animal feeding conditions, and were provided with food (Keaoxieli certified Rodent Diet). Cage, bedding, feed and drinking water were autoclaved. Cages were placed in the laminar flow rack with the cleanliness of 100, 3-5 animals per cage, and cages were replaced twice a week. The temperature in animal room is 21 to 25° C., with the relative humidity between 40% and 70%.

2. Tumor Cell Line

The murine breast cancer cancer cell line 4T1 was obtained from American Type Culture Collection (ATCC), and maintained by HD Biosciences. Cells were maintained in DMEM with 10% fetal bovine serum in a atmosphere of 5% $CO_2$ at 37° C. Passaging ratio was between 1:5 and 1:8, at the frequency of 3 to 4 times per week.

3. Construction of 4T1 Tumor Transplanting Model

4T1 murine breast tumor model was established in female Balb/c mice by subcutaneous inoculation with $1\times10^6$ cells per animal. The rate of tumor formation was 100%. Three days post cell inoculation, the cell inoculated mice were randomly sorted into treatment groups by weight. Animals in each group were administered according to Table 2.

TABLE 2

Experimental Design for 4T1

| Group | Treatment | N | Route of Administration | Dosing Level | Schedule |
|---|---|---|---|---|---|
| 1 | Vehicle (negative control) | 10 | i.m | 0.2 mL/mouse | q3d, total 6 dosing |
| 2 | Docetaxel (positive control) | 10 | i.v | 10 mg/kg | QW, total 3 dosing |
| 3 | The composition YS-ON-001 | 10 | i.m | 0.1 mL/mouse | q3d, total 6 dosing |
| 4 | The composition YS-ON-001 | 10 | i.m | 0.2 mL/mouse | q3d, total 6 dosing |

Group 1: In vehicle group, DPBS was injected into both hind legs at 0.1 mL/site.
Group 3: YS-ON-001 low dose group, 0.1 mL of YS-ON-001 was injected into right hind leg and 0.1 mL of DPBS was injected into left hind leg in 0,1 mL/mouse
Group 4: YS-ON-001 high dose group, YS-ON-001 was injected into both hind legs at 0.1 mL/site, in total 0.2 mL.

II. Test Method
1. Test groups

There were 4 groups: Vehicle group, Docetaxel group, YS-ON-001 low dose group, and YS-ON-001 high dose group.

2. The Studies were Terminated when the Average Tumor Volume in Vehicle Group Reached 2500 $mm^3$ 3. At the end of study, the tumor mass was removed and photographed. The tumor weight was recorded. The thymus and spleen was removed and weighed. And then, the organ index was calculated.

III. Observational Indices: Same as in Example 2 Section III.

IV. Data Presentation and Analysis

Data were reported as Mean±SEM. Comparison between groups was analysed using ANOVA.

V. Results
1. Tumor Volume

Figure 8:
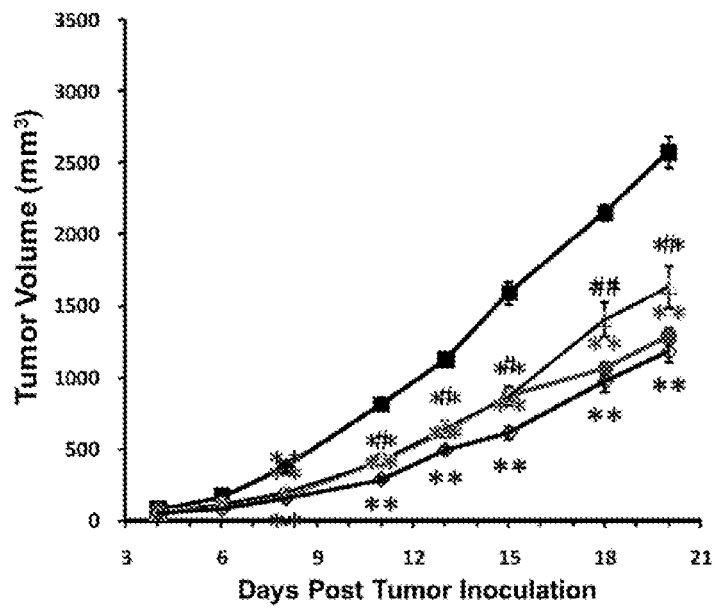
FIG. 8. Tumor volume of 4T1 tumor-bearing mice after treatment. ■Vehicle control group, •Docetaxel group, ΔYS-ON-001 low dose group, ◇YS-ON-001 high dose group. Bar represented SEM. **: p<0.01 vs. vehicle control group. #: p<0.05 vs. YS-ON-001 high dose group. ##: p<0.01 vs. YS-ON-001 high dose group.

A graphical presentation of the effect of YS-ON-001 on 4T1 murine breast tumor volume is shown in FIG. 8.

Figure 9:
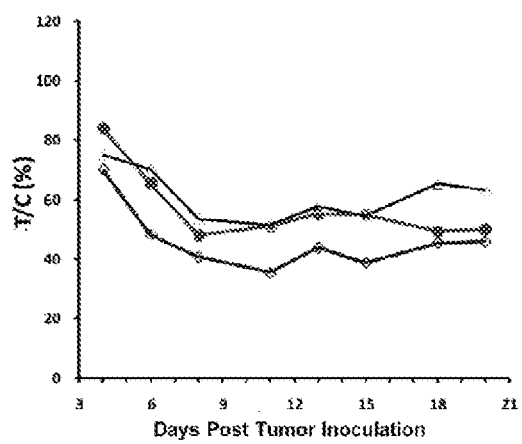
FIG. 9. Relative tumor proliferation rate (T/C) of 4T1 tumor-bearing mice after treatment. •Docetaxel group, ΔYS-ON-001 low dose group, ◇YS-ON-001 high dose group.

A graphical presentation of the effect of YS-ON-001 on 4T1 murine breast tumor proliferation rate is shown in FIG. 9.

Take the day of the tumor as Day 0. On Day 3, animals were randomized by body weight and administered according to group assignment.

Tumors in the vehicle control group grew progressively in all ten mice. At the end of study, the mean tumor volume reached 2576±108 mm$^3$.

Treatment with Docetaxel significantly inhibited the tumor growth starting from Day 8 till end of the study, resulting in a relative tumor proliferation rate of 50.12%, with a significant difference compared to the vehicle control group. ($p<0.01$).

YS-ON-001 treatment significantly inhibit tumor growth starting from Day 8 till end of the study compared to vehicle control group ($p<0.01$). There is a significant difference between YS-ON-001 low dose group and high dose group from Day 11 till end of the study ($p<0.05$). The relative tumor proliferation rate at the end of the study is 63.43% and 45.87%, respectively.

2. Tumor Weight

Figure 10:
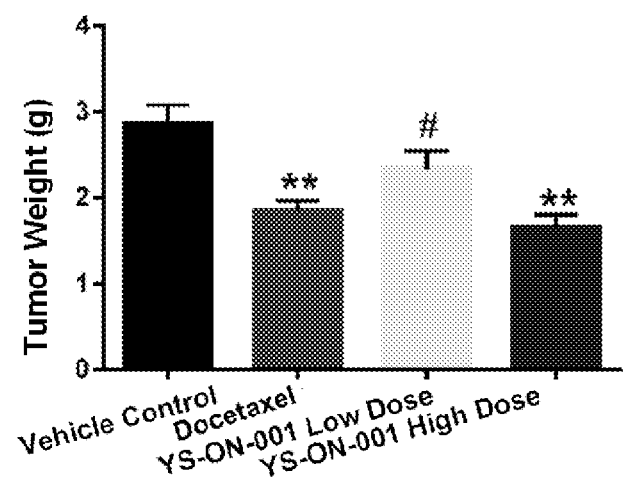
FIG. 10. Tumor weight of 4T1 tumor-bearing mice after treatment. Bar represented SEM. **: p<0.01 vs. vehicle control group. #: p<0.05 vs. YS-ON-001 high dose group.

A graphical presentation of the effect of YS-ON-001 on 4T1 murine breast tumor weight is shown in FIG. 10.

At the end of study, the tumor mass was removed and weighed. Similar with tumor volume, Treatment with Docetaxel significantly lower the tumor weight compared to the vehicle control group ($p<0.01$). YS-ON-001 high dose group significant decreased tumor weight when compared to the vehicle control group ($p<0.01$). YS-ON-001 low dose group slightly lowered tumor weight when compared to the vehicle control group. The tumor weight in YS-ON-001 high dose group is significantly lower than that in YS-ON-001 low dose group ($p<0.05$). The inhibition rate is 35.55%, 18.21%, and 42.26%, for Docetaxel group, YS-ON-001 low dose and high dose group, respectively.

3. Body Weight

Figure 11:
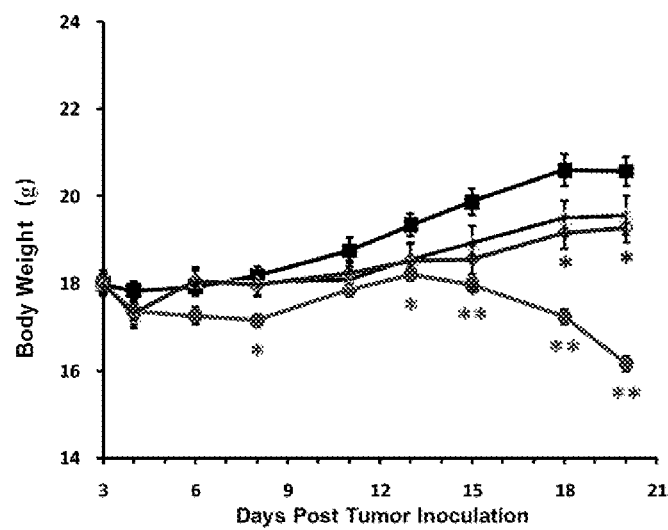
FIG. 11. Body weight of 4T1 tumor-bearing mice after treatment. ■Vehicle control group, •Docetaxel group, ΔYS-ON-001 low dose group, ◇YS-ON-001 high dose group. Bar represented SEM. *: p<0.05 vs. vehicle control group. **: p<0.01 vs. vehicle control group.
Figure 12:
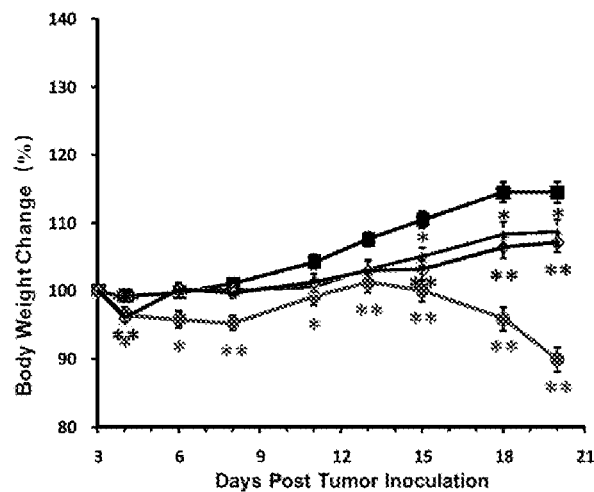
FIG. 12. Body weight change of 4T1 tumor-bearing mice after treatment. ■Vehicle control group, •Docetaxel group, ◇YS-ON-001 low dose group, ◇YS-ON-001 high dose group. Bar represented SEM. *: p<0.05 vs. vehicle control group. **: p<0.01 vs. vehicle control group.

A graphical presentation of the effect of YS-ON-001 on body weight and body weight changes of 4T1 murine breast tumor is shown in FIGS. 11 & 12.

The average body weight (BW) was significantly affected by the treatment of Docetaxel compared to the vehicle group on Day 8 and from Day 13 to end of study ($p<0.01$). The average body weight change was significantly reduced by the treatment of Docetaxel compared to the vehicle group from Day 4 to end of study ($p<0.05$). The weight at the end of the study also showed a downward trend compared to that in the same group at the time of grouping.

The mouse body weight was not obviously effected in YS-ON-001 low dose group compared to vehicle group. The body weight in YS-ON-001 high dose group was significantly lower from Day 15 than that in vehicle group ($p<0.05$). The body weight change in two YS-ON-001 groups was significantly lower on Day 4 and from Day 15 to end of study compared to vehicle control group ($p<0.05$ for low dose group, $p<0.01$ for high dose group). However the body weight was still increased compared to that in the same group at the time of grouping.

4. Thymus and Spleen Weight

Figure 13A:
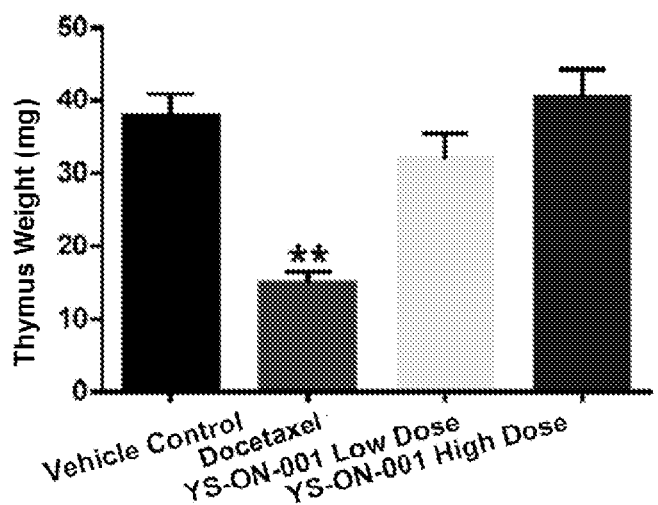
FIGS. 13A & 13B. Thymus weight and thymus index of 4T1 tumor-bearing mice after treatment. *: p<0.05 vs. vehicle control group. **: p<0.01 vs. vehicle control group.
Figure 13B:
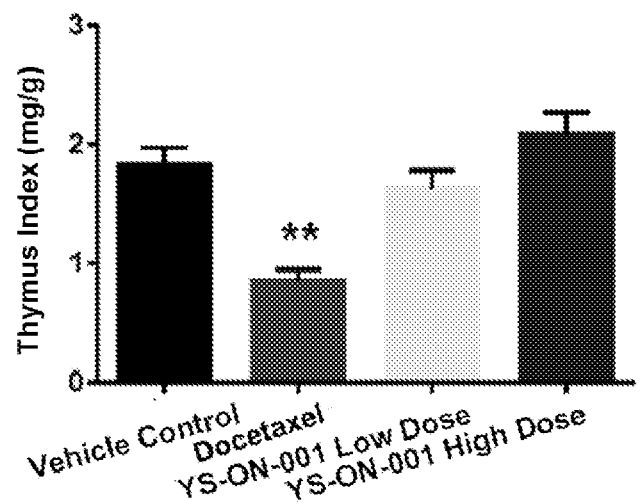
Figure 14A:
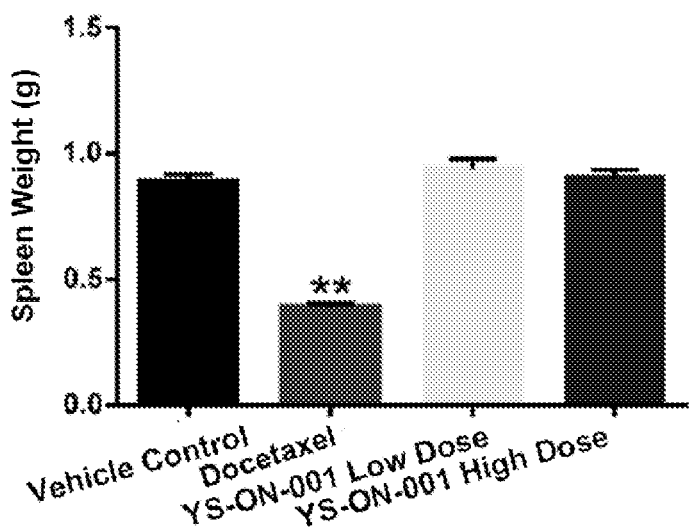
FIGS. 14A & 14B. Spleen weight and spleen index of 4T1 tumor-bearing mice after treatment. *: p<0.05 vs. vehicle control group. **: p<0.01 vs. vehicle control group.
Figure 14B:
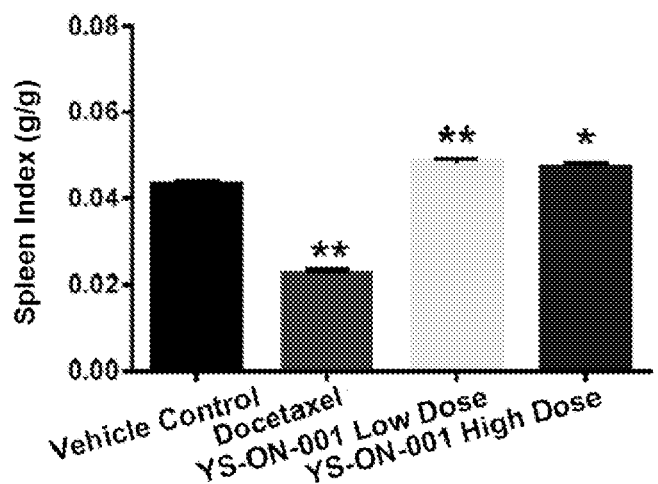

A graphical presentation of the thymus and spleen weight as well as organ index of 4T1 murine breast tumor is shown in FIGS. 13 & 14.

At the end of study, except tumor mass, the thymus and spleen was removed and weighed.

Compared to the vehicle group, Docetaxel treatment significantly reduced thymus and spleen weight and thymus and spleen index ($p<0.01$). The thymus weight, spleen weight and thymus organ index were not affected by the treatment of YS-ON-001 compared to the vehicle group. In both dose of YS-ON-001 groups, the spleen organ index was increased compared to the vehicle group significantly ($p<0.01$ for low dose group, $p<0.05$ for high dose group).

VI. Discussion and Conclusion

In the present example, the vehicle control group had a strong tumor growth and the Docetaxel group showed a significant inhibitory effect on tumor growth as a positive control.

YS-ON-001 showed anti-tumor activity in a dose-dependent manner when used as a single agent at 0.1 mL/mouse and 0.2 mL/mouse. Moreover, the animals were well tolerated and showed no significant effect on thymus weight. The antitumor effect of high dose group was comparable to that of Docetaxel group, with significantly reduced side effects.

In the present example, the spleen index in two YS-ON-001 groups increased compared to that in vehicle control group. Further analysis is needed to understand the cause. Preliminary judgment may be enhanced immune function resulting weight increasing in immune organ.

The results showed that YS-ON-001 showed inhibitory effect in a dose-dependent manner on tumor growth at the tested dose level in 4T1 breast cancer animal model. Meanwhile the tumor-bearing mice showed no obvious side effects.

Example 4. Therapeutic Effects of the Composition (YS-ON-001) Alone or Combined with Sorafenib in Subcutaneous H22 Murine Hepatocellular Carcinoma Model I. Construction of Tumor Model 1. Animals and animal husbandry were the same as in Example 2.

2. Tumor Cell Line

The murine hepatocellular carcinoma cell line H22 was obtained from China Center for Type Culture Collection (CCTCC) and maintained by HD Biosciences. Cells were maintained in Balb/c mice as ascites. The passage interval is 7-8 days.

3. Construction of H22 Tumor Transplanting Model

The donor mice with H22 ascites were sacrificed and sterilized by 75% alcohol immersion. The ascites was collected and re-suspended in pre-cooled DPBS at appropriate density. H22 murine hepatocellular carcinoma tumor model was established in female Balb/c mice by subcutaneous inoculation with $5 \times 10^6$ cells per animal. The rate of tumor formation was 100%. Three days post cell inoculation, the cell inoculated mice were randomly sorted into treatment groups by weight. Animals in each group were administered according to Table 3.

II. Test Method

1. Test Groups

There were 4 groups: Vehicle group, Sorafenib group, YS-ON-001 group, and Sorafenib+YS-ON-001 group.

TABLE 3

Experimental Group and Dosage

| Group | Treatment# | N | Route of Administration* | Dosing Level | Schedule |
|---|---|---|---|---|---|
| 1 | Vehicle* | 10 | i.m./s.c | 0.2 mL/mice | BID |
| 2 | Sorafenib | 10 | p.o. | 60 mg/kg | QD |
| 3 | The composition YS-ON-001 | 10 | i.m./s.c | 0.2 mL/mice | BID |
| 4 | Sorafenib + the composition YS-ON-001 | 10 | p.o + i.m./s.c | 60 mg/kg + 0.2 mL/mice | BID + QD |

*Vehicle was DPBS.
Sorafenib was administration via oral gavage, vehicle and YS-ON-001 was injected 0.1 mL by i.m. and 0.1 mL by s.c..

2. The Studies were Terminated when the Average Tumor Volume in Vehicle Group Reached 2500 mm$^3$ 3. At the end of study, the tumor mass was removed and photographed. The tumor weight was recorded.

III. Observational Indices: Same as in Example 2.

IV. Results

1. Tumor Volume

Figure 15A:
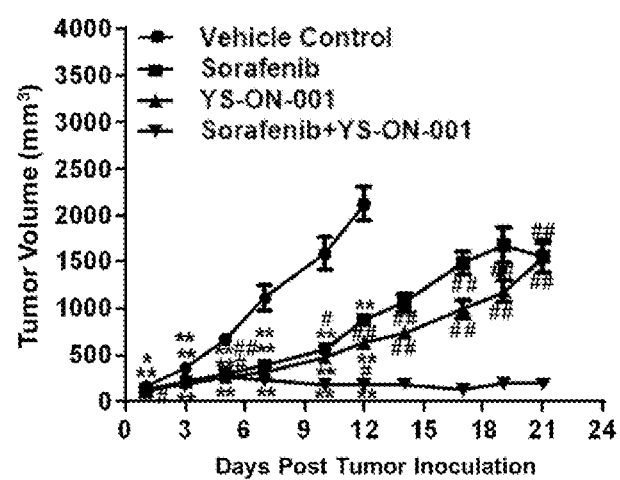
FIG. 15A. Tumor volume of H22 tumor-bearing mice during treatment. Bar represented SEM. *: p<0.05 vs. vehicle control group. **: p<0.01 vs. vehicle control group. #: p<0.05 vs. Sorafenib+YS-ON-001 group. ##: p<0.01 vs. Sorafenib+YS-ON-001 group.

A graphical presentation of the effect of YS-ON-001on H22 murine hepatocellular carcinoma tumor volume is shown in FIG. 15A.

Figure 15B:
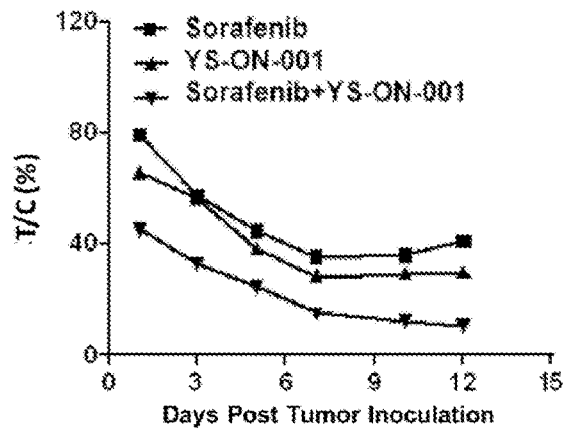
FIG. 15B. Relative tumor proliferation rate (T/C) of H22 tumor-bearing mice during treatment.

A graphical presentation of the effect of YS-ON-001on H22 murine hepatocellular carcinoma tumor proliferation rate is shown in FIG. 15B.

Take the day of the tumor as Day 0. On Day 3, animals were randomized by body weight and administered according to group assignment.

Tumors in the vehicle-treated control group grew progressively in all ten mice. When the vehicle group was terminated on Day 12, the mean tumor volume reached 2120±182 mm$^3$.

One mouse in the vehicle group and two mice in Sorafenib group were sacrificed at Day 10 and Day 19 when their tumor volume reached 2500 mm$^3$. The whole study was terminated on Day 21.

Treatment with Sorafenib significantly inhibited tumor growth from Day 3 to end of the study compared to that in vehicle control group ($p<0.01$). The relative tumor proliferation rate on Day 12 is 29.90%.

Treatment with Sorafenib+YS-ON-001 significantly inhibited tumor growth from Day 1 to end of the study compared to that in vehicle control group ($p<0.01$). The relative tumor proliferation rate on Day 12 is 10.61%.

YS-ON-001 showed strong anti-tumor activity when used BID at 0.2 mL/mouse. Sorafenib+YS-ON-001 showed a very significant inhibition of tumor growth and a significant synergistic effect. There were no animal dead due to drug toxicity in single drug group or combination drug group.

The results showed that The YS-ON-001 and combination group showed strong anti-tumor activity in H22 murine hepatocellular carcinoma tumor mouse model at the tested dosing level. Combining YS-ON-001 and Sorafenib induced strongly enhanced antitumor activity compared with either agent alone.

Example 5. Therapeutic Effects of the Composition (YS-ON-001) and PIKA Alone in Subcutaneous LL/2 Murine Lewis Lung Cancer Model in Female C57BL/6 Mice I. Construction of Tumor Model 1. Animals and Animal Husbandry were the Same as in Example 2

2. The Murine Lewis Lung Cancer Cell Line LL/2 was Obtained, Cultured and the LL/2 Murine Lewis Lung Tumor Model was Established the Same as in Example 2. Animals in each group were administered according to Table 4.

II. Test Method

1. Test Groups

There were 6 groups: Vehicle group, Cisplatin group, YS-ON-001 group, YS-ON-002 (no virus) group, Rabies vaccine group and Cisplatin+YS-ON-001 group. The difference between YS-ON-001 and YS-ON-002 is that there is no inactivated rabies virus in YS-ON-002.

TABLE 4

Experimental Group and Dosage

| Group | Treatment | N | Route of Administration | Dosing Level* | Schedule |
|---|---|---|---|---|---|
| 1 | Vehicle | 10 | i.m. | 0.2 mL/mouse | Q2D, total 7 times |
| 2 | Cisplatin | 10 | i.v. | 5 mg/kg | Q2D, total 2 times |
| 3 | The composition YS-ON-001 | 10 | i.m. | 0.2 mL/mouse | Q2D, total 7 times |
| 4 | YS-ON-002 (PIKA alone) | 10 | i.m | 0.2 mL/mouse | Q2D, total 7 times |
| 5 | Rabies Vaccine (Vero Cell) | 10 | i.m. | 0.2 mL/mouse | Q2D, total 7 times |
| 6 | Cisplatin + the composition YS-ON-001 | 10 | i.v. + i.m. | 0.2 mL/mouse | QW (total 2 times) + Q2D (total 7 times) |

*In vehicle group, DPBS was injected into both hind legs at 0.1 mL/site. YS-ON-001 and YS-ON-002 were injected into both hind legs at 0.1 mL/site.

There are significant differences in tumor volume between Sorafenib group and Sorafenib+YS-ON-001 group on Day 1, Day 5 and from Day 10 to end of the study ($p<0.05$ or $p<0.01$).

There are significant differences in tumor volume between YS-ON-001 group and Sorafenib+YS-ON-001 group on Day 5 and from Day 10 to end of the study ($p<0.05$ or $p<0.01$).

V. Discussion and Conclusion

In the present example, the vehicle control group had a strong tumor growth and the Sorafenib group showed a significant inhibitory effect on tumor growth as a positive control. These indicate that the results are reliable.

2. The Studies were Terminated when the Average Tumor Volume in Vehicle Group Reached 2500 mm$^3$ 3. At the end of study, the tumor mass was removed and photographed. The tumor weight was recorded.

III. Observational Indices

1. Tumor Volume

The measure and calculation of tumor volume, tumor weight were same as in Example 2.

2. Combination Drug Index

Q value was calculated according to Jin's formula, $Q=0.85\text{-}1.15$ for the additional effect, $Q>1.15$ for the synergetic effect:

$$Q=Ea+b/(Ea+Eb-Ea\times Eb)$$

Where Ea+b is the tumor inhibition rate in drug combination group, Ea and Eb are the tumor inhibition rates in single drug group.

IV. Results

1. Tumor Volume

Figure 16A:
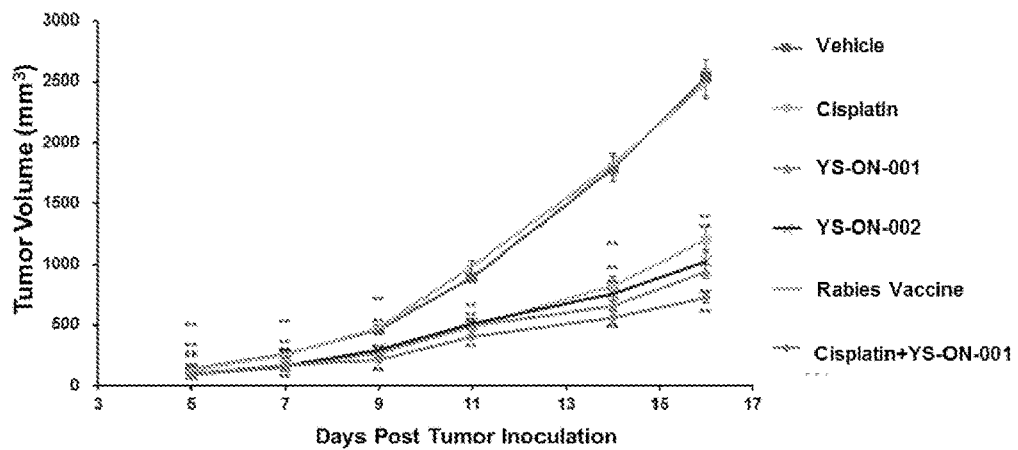
FIG. 16A. Tumor volume of LL/2 tumor-bearing mice after treatment. Bar represented SEM. **: p<0.01 vs. vehicle control group.

A graphical presentation of the effect of YS-ON-001, YS-ON-002 and the combination group on tumor volume of the mice bearing LL/2 murine Lewis lung carcinoma is shown in FIG. 16A.

Figure 16B:
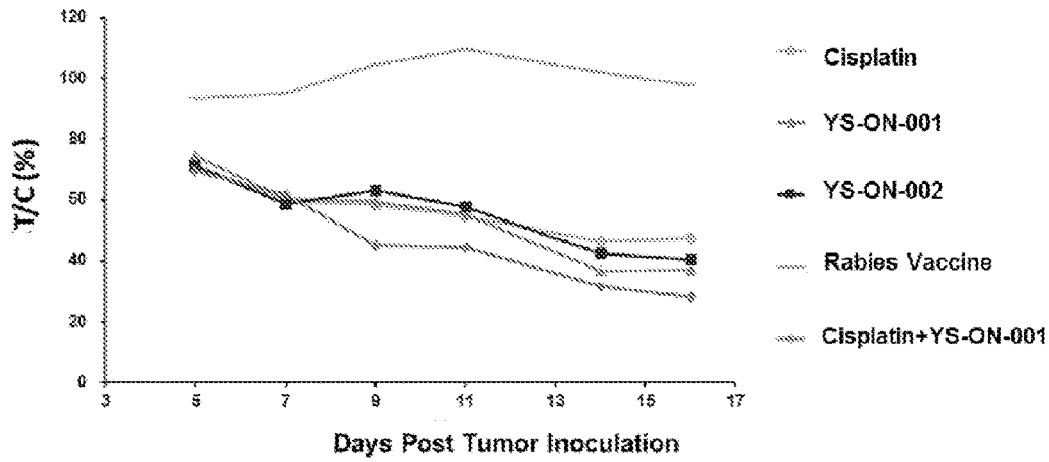
FIG. 16B. Relative tumor proliferation rate (T/C) of LL/2 tumor-bearing mice after treatment.

A graphical presentation of the effect of YS-ON-001, YS-ON-002 and the combination group on tumor proliferation rate of the mice bearing LL/2 murine Lewis lung carcinoma is shown in FIG. 16B.

Take the day of the tumor as Day 0. On Day 3, animals were randomized by body weight and administered according to group assignment.

Tumors in the vehicle control group grew progressively in all ten mice. When the vehicle group was terminated, the mean tumor volume reached 2535±148 mm$^3$.

Treatment with Cisplatin significantly inhibited the tumor growth compared with the vehicle control group from day 5 to the end of the study ($p<0.01$), resulting in a relative tumor proliferation rate of 47.46%.

Treatment with YS-ON-001 and YS-ON-002 significantly inhibited tumor growth when compared to the vehicle control group from day 5 to the end of study ($p<0.01$). The relative tumor proliferation rate was 37.02% and 40.56%, respectively.

Treatment with Rabies Vaccine had no obvious affect compared with vehicle control group ($p>0.05$). The relative tumor proliferation rate was 97.87% at the end of the study.

The combination group significantly inhibited tumor growth when compared with the vehicle control group from day 5 to the end of the study ($p<0.01$). The relative tumor proliferation rate was 28.38% at the end of the study. The relative tumor proliferation rate was lower than that in Cisplatin and YS-ON-001 alone groups. According to Jin's formula, YS-ON-001 and Cisplatin had additional effect, Q=0.87.

The tumor volume of YS-ON-001 group is lower than YS-ON-002 group, however the difference is statistically insignificant. The tumor volume of YS-ON-001 group is lower than YS-ON-002 group from Day 5 to end of the study.

According to Jin's formula, rabies virus and other components in the composition have additional effect, Q=0.93.

2 Tumor Weight

Figure 17:
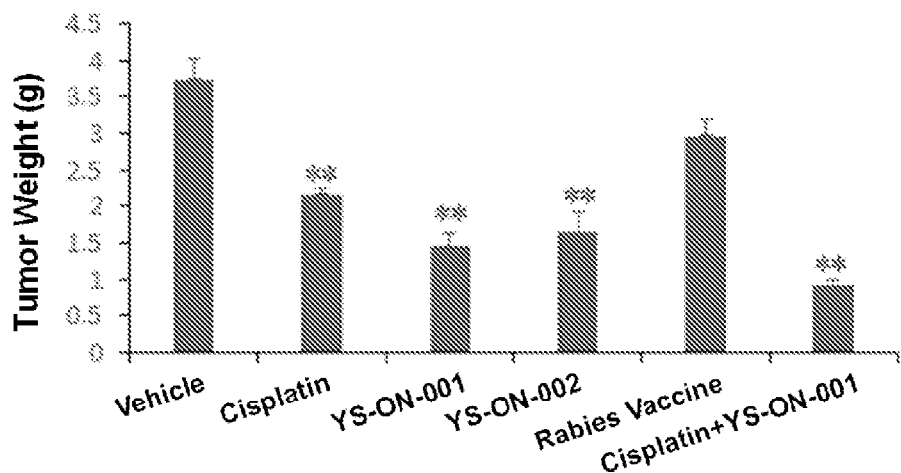
FIG. 17. Tumor weight of LL/2 tumor-bearing mice after treatment. Bar represented SEM. **: p<0.01 vs. vehicle control group.

A graphical presentation of the effect of YS-ON-001, YS-ON-002 and the combination group on tumor weight of the mice bearing LL/2 murine Lewis lung carcinoma is shown in FIG. 17.

At the end of study, the tumor mass was removed and weighed. Similar to the effect on tumor volume, Cisplatin, YS-ON-001, YS-ON-002 and the combination group had significantly decreased tumor weight when compared with the vehicle control group ($p<0.01$), resulting in 42.38% 60.88, 56.04% and 75.44% tumor inhibition rates, respectively.

According to Jin's formula, rabies virus and other components in the composition have additional effect, Q=0.97.

V. Discussion and Conclusion

In the present example, the vehicle control group had a strong tumor growth and the cisplatin group showed a significant inhibitory effect on tumor growth as a positive control. These indicate that the results are reliable.

YS-ON-001 and YS-ON-002 showed strong anti-tumor activity when used as a single agent at 0.2 mL/mouse administrated i.m on LL/2 murine Lewis lung tumor model. The animals were well tolerated and had a slight effect on the body weight, however the toxic side effects were significantly lower than the control drug Cisplatin. The anti-tumor effect was comparable with the control drug Cisplatin.

The combination group's relative tumor proliferation rate was 28.38%, which was lower than the groups treated with Cisplatin and YS-ON-001 alone. According to Jin's formula, YS-ON-001 and Cisplatin had additional effect.

There are no statistically significant variations in tumor inhibit effect between YS-ON-001 and YS-ON-002, however rabies virus and other components in the composition have additional effect according to Jin's formula.

The results showed that YS-ON-001 and YS-ON-002 showed inhibitory effect at the tested dose level in LL/2 Lewis lung cancer animal model. The composition YS-ON-001 and Cisplatin had additional effect Example 6. Therapeutic Effects of the Composition (YS-ON-001) in B16F10 Tumor Metastasis Model in Female C57BL/6 Mice I. Construction of Tumor Model 1. Animals and Animal Husbandry were the Same as in Example 2

2. Tumor Cell Line

The cell line B16F10 was obtained from American Type Culture Collection (ATCC) and maintained by HD Biosciences. Cells were maintained in DMEM with 10% fetal bovine serum in an atmosphere of 5% $CO_2$ at 37° C. Passaging ratio was between 1:5 and 1:8, at the frequency of 3 to 4 times per week.

on a 12-hour light/dark cycle.

3. Construction of LL/2 Tumor Transplanting Model

B16F10 metastasis tumor model was established in female C57BL/6 mice by intravenous inoculation with 5×10$^4$/0.2 mL per animal. One day post cell inoculation, mice were randomly sorted into treatment groups by weight. Animals in each group were administered according to Table 5.

II. Test Method

1. Test Groups

There were 3 groups: Vehicle group, Cisplatin group and YS-ON-001 group.

TABLE 5

Experimental Group and Dosage

| Group | Treatment | N | Route of Administration[#] | Dosing Level | Schedule |
|---|---|---|---|---|---|
| 1 | Vehicle* | 10 | i.m./s.c. | 0.2 mL/mice/dose | BID |
| 2 | Cisplatin | 10 | i.v. | 5 mg/kg | Q4D |
| 3 | The composition YS-ON-001 | 10 | i.m./s.c. | 200 µg/0.2 mL/mice/dose | BID |

*Vehicle is DPBS
[#]Animals in vehicle group and YS-ON-001 group was dosed of 0.1 mL via i.m. (hind leg) and s.c. injection, respectively.

2. At the end of the study, the studies were terminated on day 15. The lung was removed and photographed. The number of metastasis spot was counted. The thymus and spleen were removed, weighed and calculated for organ indices.

III. Observational Indices

1. Body Weight

Body weight of each mouse was weighed three times a week. Body weight change (BWC) was calculated as:

$$BWC=(BW_n-BW_0)/BW_0 \times 100\%$$

Where BWn is the BW at Day n and $BW_0$ is the BW at the day when the treatment was initiated.

2. Number of Lung Metastases

At the end of study, the animals were sacrificed and the lung was removed. And then, the metastasis number was counted.

3. Thymus and Spleen Weight

At the end of the study, the thymus and the spleen were removed and weighed.

IV. Data Presentation and Analysis

Data were reported as Mean±SEM. Comparison between groups was analysed using ANOVA.

V. Results

1. Body Weight

Figures 18A, 18B:
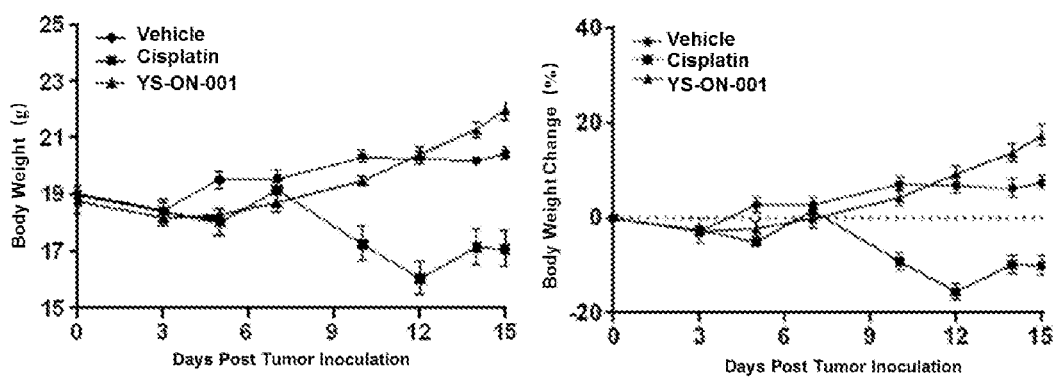
FIGS. 18A & 18B. Body weight of B16F10 tumor-bearing mice post treatment. Bar represented SEM. *: p<0.05 vs. vehicle control group. **: p<0.01 vs. vehicle control group.

A graphical presentation of the effect of YS-ON-001 on body weight and body weight changes of the mice is shown in FIGS. 18A & 18B.

The average body weight (BW) was significantly lowered by the treatment of Cisplatin compared with the vehicle group ($p<0.01$) from Day 5 to the end of the study (except day 7). A similar result was observed in the body weight change.

In YS-ON-001 group, the body weight was transiently slightly lowered compared to vehicle control group. However, on Day 5 and Day 15, the body weight in YS-ON-001 group was significantly lowered compared to vehicle control group.

2 Number of Lung Metastases

Figure 19:
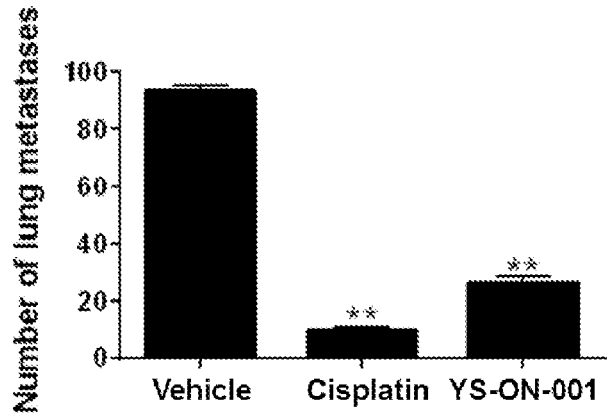
FIG. 19. Number of lung metastases of B16F10 tumor-bearing mice post treatment. Bar represented SEM. **: p<0.01 vs. vehicle control group.
Figure 20A:
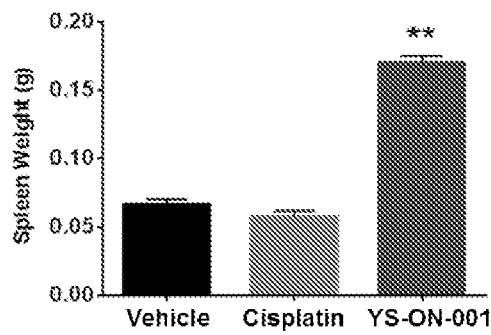
FIG. 20A-20D. Thymus and spleen weight of B16F10 tumor-bearing mice post treatment. Bar represented SEM. *: p<0.05 vs. vehicle control group. **: p<0.01 vs. vehicle control group.
Figure 20B:
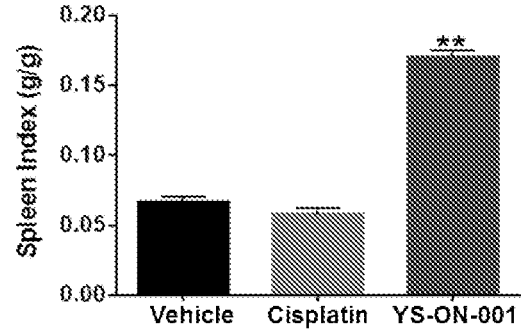
Figure 20C:
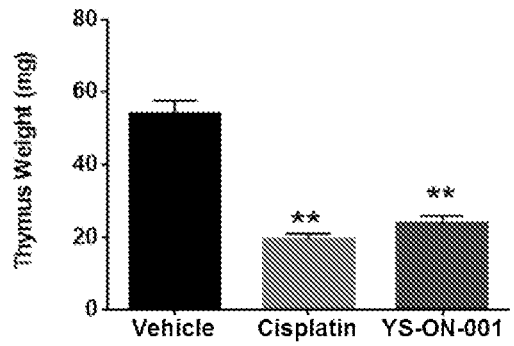
Figure 20D:
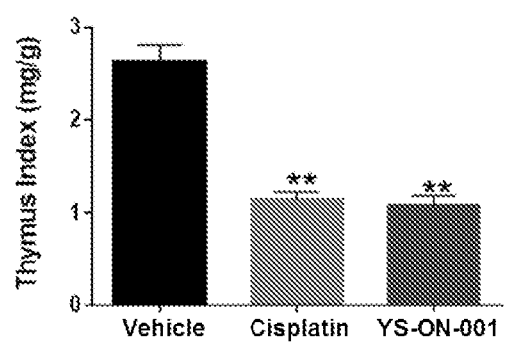

A graphical presentation of the effect of YS-ON-001 on number of lung metastasis of the mice is shown in FIG. 19.

At the end of study, the animals were sacrificed and the lung was removed. And then, the metastasis number was counted.

Compared with vehicle group, the number of lung metastases significantly decreased by treatment with Cisplatin and YS-ON-001 ($p<0.01$).

3 Thymus and Spleen Weight

A graphical presentation of the thymus and spleen weight as well as each organ index of the mice is shown in FIG. 20.

At the end of the study, in addition to lung, the thymus and spleen were removed and weighed. The organ indices for each organ were calculated.

Compared with the vehicle group, treatment with Cisplatin significantly decreased thymus weight ($p<0.01$), thymus index ($p<0.01$), while spleen weight and spleen index was not affected.

Compared with the vehicle group, the thymus weight and thymus index was significantly decreased by treatment with YS-ON-001 ($p<0.01$), while the spleen weight and spleen index was significantly increased ($p<0.01$).

VI. Discussion and Conclusion

In the present example, the lung metastases were observed in all animals in vehicle control group, resulting in the average number of lung metastases at 93.43±1.76. The average number of lung metastases was significantly reduced in Cisplatin group. These indicate that the results are reliable.

The YS-ON-001 showed strong anti-metastasis activity with significantly reduced average number of lung metastases in B16F10 tumor metastasis model at the tested dosing level.

Example 7. Therapeutic Effects of the Composition (YS-ON-001) in S180 Tumor Model in Female Balb/C Mice I. Construction of Tumor Model 1. Animals and animal husbandry were the same as in Example 2

2. Tumor Cell Line

The cell line S180 was obtained from the Cell Bank of Chinese Academy of Medical Sciences and maintained in IPE-CAS laboratory. Cells were maintained in Balb/c mice as ascites. The passage interval is 5-6 days.

3. Construction of S180 Tumor Transplanting Model

Balb/c animals were fed for 5 to 7 days, and S180 tumor was intraperitoneal inoculated into the F0 generation mice. The ascites were taken out when the abdominal cavity to a certain extent, and then inoculated in F1 generation mice. The tests used F2-F3 generation mice. S180 tumor model was established in female Balb/c mice by subcutaneous inoculation with cell suspension ($2 \times 10^6/0.2$ mL/animal). Two days post cell inoculation, the cell inoculated mice were randomly sorted into treatment groups. Animals in each group were administered according to Table 6.

II. Test Method

1. Test Groups

There were 3 groups: Vehicle group, Cyclophosphamide (CTX) group, and YS-ON-001 group.

TABLE 6

| Experimental Group and Dosage | | | | | |
|---|---|---|---|---|---|
| Group | Treatment | N | Route of Administration | Dosing Level | Schedule |
| 1 | Normal Saline | 10 | i.m. | 0.2 mL/mice/dose | Q2D, in total 10 times |
| 2 | Cyclophosphamide (CTX) | 10 | i.p. | 20 mg/kg | Q2D, in total 10 times |
| 3 | The composition YS-ON-001 | 10 | i.m | 0.2 mL/mice/dose | Q2D, in total 10 times |

2. At the end of the study, the studies were terminated on day 21. The tumor was removed and photographed. The weight of tumor was recorded.

III. Observational Indices

1. Tumor Volume

The anti-tumor effect of the test article was observed by measuring tumor diameter. Tumor volumes were measured 3 times weekly and the relative tumor proliferation rate T/C (%) was calculated.

1.1 Tumor volume (TV) was calculated as follow:

$$TV = \frac{1}{2} \times a \times b^2$$

where a and b denote long and wide, respectively.

2. At the end of study, tumor mass was removed and weighed.

IV. Data Presentation and Analysis

Data were reported as Mean±SEM. Comparison between groups was analysed using ANOVA.

V. Results

1. Tumor Volume

Figure 21:
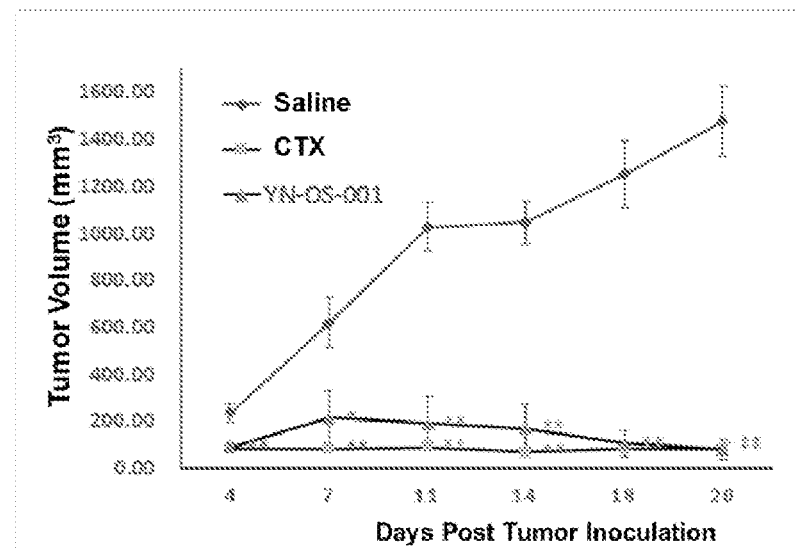
FIG. 21. Tumor volume of S180 tumor-bearing mice during treatment. Bar represented SEM. **: p<0.01 vs. vehicle control group.

A graphical presentation of the effect of YS-ON-001 group on tumor volume of S180 tumor model in female Balb/C mice is shown in FIG. 21.

Tumors in the saline-treated control group grew progressively in all ten mice. At day 21, the mean tumor volume reached 2000 mm$^3$.

Treatment with CTX significantly inhibited the tumor growth compared with the saline control group from day 4 to the end of the study (p<0.01).

Treatment with YS-ON-001 significantly inhibited tumor growth when compared to the saline control group from day 4 to the end of study (p<0.01). The tumor volume in YS-ON-001 group was similar to that in CTX group.

2 Tumor Weight

Figure 22:
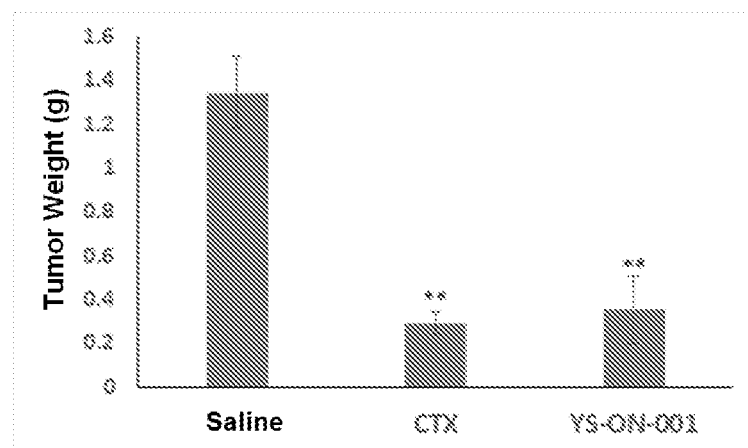
FIG. 22. Tumor weight of S180 tumor-bearing mice after treatment. Bar represented SEM. **: p<0.01 vs. vehicle control group.

A graphical presentation of the effect of YS-ON-001 on tumor weight of S180 tumor model in female Balb/C mice is shown in FIG. 22.

At the end of study, the tumor mass was removed and weighed. Similar to the effect on tumor volume, CTX and YS-ON-001 had significantly decreased tumor weight when compared with the saline control group (p<0.01).

VI. Discussion and Conclusion

In the present example, the vehicle control group had a strong tumor growth and the CTX group showed a significant inhibitory effect on tumor growth as a positive control.

Treatment with YS-ON-001 significantly inhibited tumor growth with significantly reduced tumor volume and tumor weight.

The results showed YS-ON-001 showed strong anti-tumor activity in S180 tumor model at the tested dosing level.

Example 8. Therapeutic Effects of the Composition (YS-ON-001) in Ehrlich Ascites Cancer (EAC) Tumor Model in Female Balb/C Mice I. Construction of Tumor Model 1. Animals 1.1 Female Kunming mice (5-6 weeks old) were obtained and tested after 5-6 days adaptive feeding.

1.2 Animal Husbandry

Animals were feed according to the SPF level animal feeding conditions, and were provided with food (Keaoxieli certified Rodent Diet). Cage, bedding, feed and drinking water were autoclaved. Cages were placed in the laminar flow rack with the cleanliness of 100, 3-5 animals per cage, and cages were replaced twice a week. The temperature in animal room is 21 to 25° C., with the relative humidity between 40% and 70%.

2. Tumor Cell Line

The Ehrlich Ascites Cancer (EAC) tumor cell line EAC was obtained from the Cell Bank of Chinese Academy of Medical Sciences and maintained in IPE-CAS laboratory. Cells were maintained in Kunming mice as ascites. The passage interval is 7-8 days.

3. Construction of Tumor Transplanting Model

Animals were fed for 5 to 7 days, and EAC tumor was intraperitoneal inoculated into the F0 generation mice. The ascites were taken out when the abdominal cavity to a certain extent, and then inoculated in F1 generation mice. The tests used F2-F3 generation mice. EAC tumor model was established in female Kunming mice by intraperitoneal inoculation with cell suspension (1×10$^6$/0.2 mL/animal). Two days post cell inoculation, the cell inoculated mice were randomly sorted into treatment groups. Animals in each group were administered according to Table 7.

TABLE 7

Experimental Design for EAC

| Group | Treatment | N | Route of Administration | Dosing Level | Schedule |
|---|---|---|---|---|---|
| 1 | Vehicle | 10 | i.m. | 0.2 mL/mouse | Q2d, total 10 dosing |
| 2 | CTX | 10 | i.m. | 20 mg/kg | Q2d, total 10 dosing |
| 3 | The composition YS-ON-001 | 10 | i.m. | 0.2 mL/mouse | Q2d, total 10 dosing |

Group 1: In vehicle group, PBS was injected into both hind legs at 0.1 mL/site.
Group 3: YS-ON-001 group, YS-ON-001 was injected into both hind legs at 0.1 mL/site, in total 0.2 mL II. Test Method 1. Test Groups There were 3 groups: Vehicle group, CTX group, and YS-ON-001 group.

2. At the end of the study, the studies were terminated on day 21. The tumor was removed and photographed. The weight of tumor was recorded.

III. Observational Indices: Duration, Tumor Growth Delay

Tumor growth delay (TGD) was calculated as (TGD)=(T−C)/C×100%, where T and C refer to the median duration (days) of individual mouse to die for the treated and control groups, respectively.

IV. Data Presentation and Analysis

Comparison between groups was analysed using ANOVA.

V. Results

Figure 23:
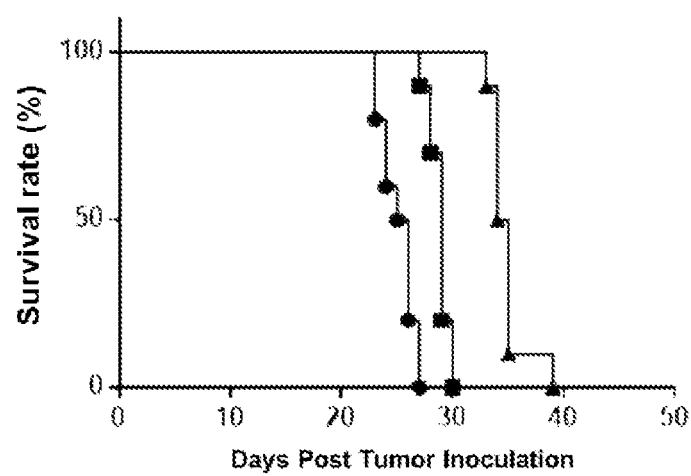
FIG. 23. Survival rate of S180 tumor-bearing mice during treatment. •Saline, ■CTX, ◆YS-ON-001.

A graphical presentation of the survival rate of EAC tumor model in female Kunming mice is shown in FIG. 23.

Take the day of the tumor inoculation as Day 0. On Day 2, animals were randomized and administered according to group assignment. Tumors in the vehicle control group grew progressively in all ten mice. Mice were observed death on Day 23, and all mice dead on Day 27. The median duration was 25.5 days.

Compared to vehicle group, mice in CTX group were observed death on Day 27, and all mice dead on Day 30. The tumor growth delay (TGD) upon treatment of CTX was 14.74%, with the median duration at 29 days.

Compared to vehicle group, mice in YS-ON-001 group were observed death on Day ee, and all mice dead on Day 39. The tumor growth delay (TGD) upon treatment of CTX was 38.65%, with the median duration at 34.5 days.

VI. Discussion and Conclusion

In the present example, the vehicle control group had a strong tumor growth and the CTX group showed a significant tumor growth delay effect as a positive control.

Treatment with the composition YS-ON-001 at 0.2 mL/mouse showed a significant tumor growth delay effect, while the animals were well tolerated. The anti-tumor effect of YS-ON-001 is significantly better than that of CTX control drug.

The results showed that YS-ON-001 showed strong anti-tumor activity and inhibitory effect on tumor growth in EAC tumor model at the tested dosing level, while the tumor-bearing mice were well tolerated.

Example 9. Therapeutic Effects of the Composition on Thyroid Cancer with Lung, Lymph Node Metastasis 1. Subject:

Mao, female, age 53, diagnosed in August 2013 with thyroid cancer with lung metastasis, undergone radical thyroidectomy. Postoperative pathology showed papillary carcinoma on thyroid left lateral lobe, with lymph node metastasis, nodular goiter on thyroid right lateral lobe. Thereafter on Oct. 28, 2013 and Feb. 6, 2014 she undergone twice iodine-131 therapy. In 2015, she undergone 4 cycles of Etoposide+Carboplatin radiotherapy (2015.09.28' 2015.10.20' 2015.11.07' 2015.12.04). After treatment, while 1-2 lesions in lung shrinked, the other 5-6 lesions unchanged, chemotherapy side effects are obvious, physical condition is poor.

2. Composition:

When administered to human subject, YS-ON-001 is formulated in sterile water for injection.

3. Administration regimen:

With the consent of patient, YS-ON-001 (1 ml) was administered through intramuscular injection at upper arm, once every 3 days, 12 doses in total.

4. Results:

In this example, subject administered with the composition of present disclosure showed no obvious side effects, all lesions are stable, and physical condition is improved.

Example 10. Therapeutic Effects of the Composition on Kidney Cancer

1. Subject:

Ma, male, age 70, November 2015 began intermittent hematuria symptom, occasional left waist pain. A comprehensive examination was performed and he was diagnosed with left kidney cancer, size about 11×12×6 cm. Chest CT suspected right lung cancer, chronic inflammation of both lungs, and may be associated with liver cysts. Considered the patient's age and family opinion, it was decided not to undergo surgery or radiotherapy and chemotherapy. He was discharged after simple anti-inflammatory treatment.

2. Composition:

When administered to human subject, YS-ON-001 is formulated in sterile water for injection.

3. Administration regimen:

With the consent of patient and his family, YS-ON-001 (2 ml) was administered through intramuscular injection at upper arm from 25th December, once every 3 days, 12 doses in total.

4. Results:

In this example, subject administered with the composition of present disclosure showed no obvious side effects, hematuria symptom and waist pain disappeared.

Example 11. Therapeutic Effects of the Composition on Gastric Adenocarcinoma with Metastatic Liver Cancer 1. Subject:

Nan, female, age 55, diagnosed in October 2015 with gastric adenocarcinoma stage IV with metastatic liver cancer, undergone Oxaliplatin+Lapatinib chemotherapy. However the chemotherapy discontinued due to significant liver damage. After receiving transaminase reduction treatment and symptomatic treatment, liver function basically back to normal.

2. Composition:

When administered to human subject, YS-ON-001 is formulated in sterile water for injection.

3. Administration regimen:

3.1 First course of treatment:

With the consent of patient, YS-ON-001 (1 ml) was administered through intramuscular injection at upper arm from 25 Dec. 2015, once every 3 days. This course was discontinued due to abnormal transaminase elevation on 29th December.

3.2 Second course of treatment:

2 Jan. 2016 liver function recovered till pre-injection level. Second course of YS-ON-001 treatment resumed from 11th January, dosage remained the same. Reviewed on 27th January.

4. Results:

After first course of treatment, transaminase abnormally elevated, suspected liver tissue necrosis caused by the administration of the composition, believed to be non-specific anti-tumor response.

After second course of treatment, patient showed no obvious side effects. Liver CT lesions showed reduced nodal shadow, proofing the conjecture of first course treatment.

Example 12. Therapeutic Effects of the Composition on Breast Cancer with Lymphatic, Lung and Osseous Metastasis 1. Subject:

Female, age 34. diagnosed in May 2008 with left breast infiltrating ductal carcinoma, undergone modified mastectomy. Case suggested lymph node metastases, immunohistochemical results showed ER−, PR++, HER2++. June 2015 confirmed both lungs and osseous metastasis. Cranial CT showed multiple metastases at bilateral cerebellar hemisphere and cerebellar vermis. The condition was judged as disease progressive disease (PD).

2. Composition:

When administered to human subject, YS-ON-001 is formulated in sterile water for injection.

3. Administration regimen:

3.1 First course of treatment:

With consent of patient, from 29 Sep. 2015 onwards YS-ON-001 was administered through intramuscular injection, one dose per week (1st, 3rd, 5th dose at 2 ml, 2nd, 4th, 6th dose at 1 ml), undergone chemotherapy on doctor's advice.

3.2 Second course of treatment:

From 14th December onwards second course of YS-ON-001 is administered through intramuscular injection, one dose (1 ml) every 3 days.

4. Results:

After first course of treatment, review by chest CT found right axillary lymph nodes swollen, pleural effusion was significantly reduced, right lung tissues recruited, necrosis on both lung's tissues, brain metastases disappeared. After a week, disease determined to be stable disease (SD).

Figure 24A:
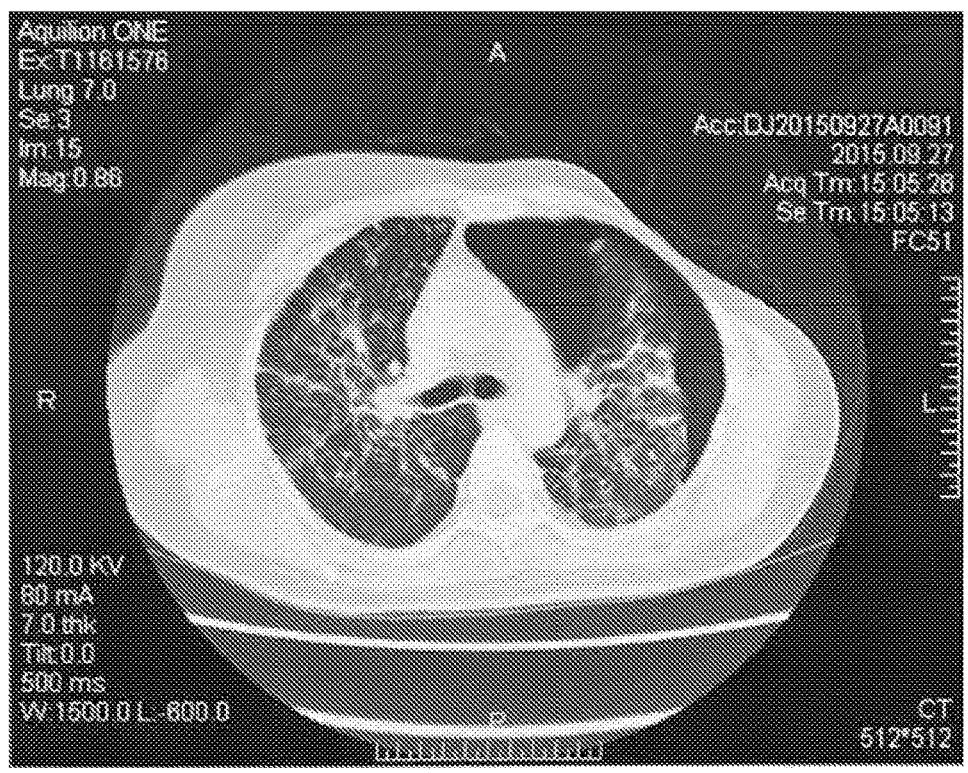
FIGS. 24A & 24B. Chest CT.
Figure 24B:
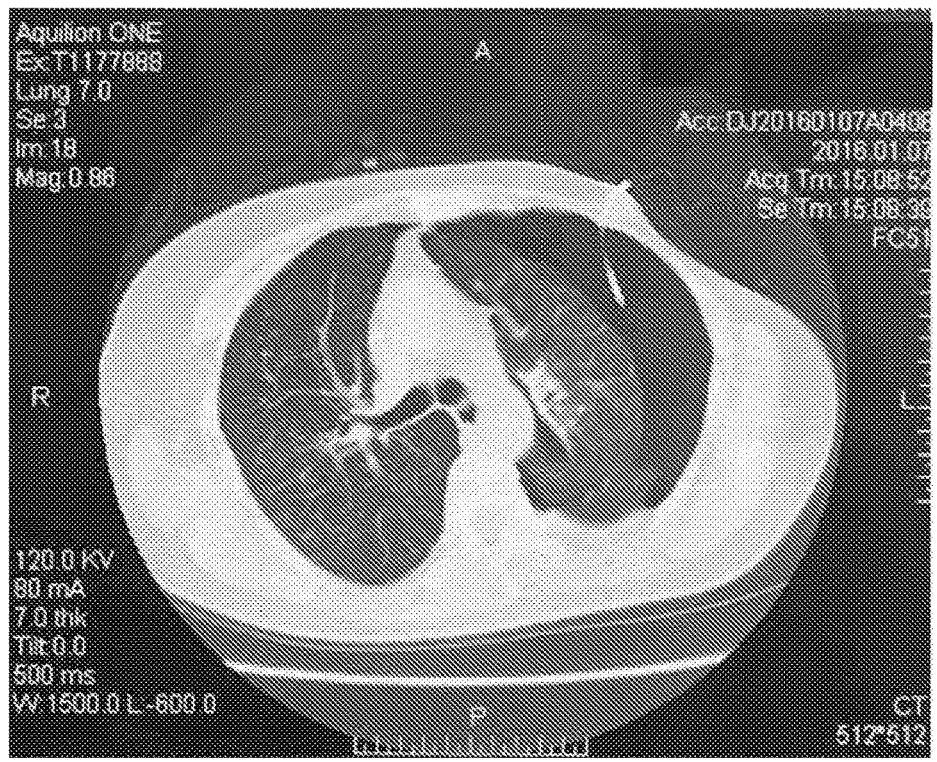

After second course of treatment, chest CT review found both pulmonary nodular shadow obviously decreased. FIG. 24A shows the CT before using YS-ON-001, and FIG. 24B shows the CT after two courses of treatment YS-ON-001. Pulmonary nodular shadow was significantly reduced by comparing the two. The composition of present disclosure has significant antitumor effects.

Example 13. Therapeutic Effects of the Composition on Tongue Cancer

1. Subject:

Zhou, female, age 78, diagnosed with tongue cancer in April 2015, undergone left tongue cancer extended excision+mandibular partial resection+tooth extraction. Postoperative pathology showed well-differentiated squamous cell carcinoma. In May 2016 left tongue cancer relapsed, undergone extended resection on left tongue recurrent carcinoma.

2. Composition:

When administered to human subject, YS-ON-001 is formulated in sterile water for injection.

3. Administration regimen:

With consent of patient, from 26 Jul. 2016 onwards YS-ON-001 was administered through buttocks intramuscular injection, 2 doses daily. After administered for 2 days, increased dosage to 4 times daily.

4. Results:

In this example, subject administered with the composition of present disclosure showed no obvious side effects. Patient declared that upper jaw ulcers depth shallowed, physical condition improved, better sleep, increased appetite, and physical strength was getting better.

Example 14. Therapeutic Effects of the Composition on Prostate Cancer with Multiple Bone Metastases 1. Subject:

Xu, male, age 81, diagnosed with prostate cancer with multiple bone metastases in January 2013.

2. Composition:

When administered to human subject, YS-ON-001 is formulated in sterile water for injection.

3. Administration regimen:

With consent of patient, from 3 Jul. 2016 onwards YS-ON-001 was administered through intramuscular injection on every other day, 2 doses each time. From 3 Aug. 2016, doses increased to 3. From 5 Aug. 2016, injection every other day, each time 4 doses. At the same time Zoladex was used as combined treatment on doctor's advice.

4. Results:

In this example, subject administered with the composition of present disclosure showed no obvious side effects, except from muscular stiffness due to long term injection. During treatment, total prostate specific antigen level reduced, improved physical condition, pain relieved. Before treatment, prostatic puncture biopsy result showed that all 10 needles tested positive and this number reduced to 5 positive out of 10 after the treatment.

Example 15. Therapeutic Effects of the Composition on Rectal Cancer

1. Subject:

Sun, male, age 63 diagnosed in, November 2012 with rectal cancer, underwent rectal cancer resection+liver biopsy. Postoperative pathology showed moderately differentiated rectal ulcer cancer, infiltrated the entire intestine wall, multiple cancer nodules seen inside mesenteric adipose tissue, visible metastatic cancer at lymph nodes, metastatic nodules seen in liver. After recovered from operation, from May 2012 onwards undergone treatment by taking Bevacizumab (600 mg) and Xelox (OXA 250 mg, Xelod3.0, 14d). After 8 cycles, taking only Bevacizumab till September 2015. During March 2016 review CT image diagnosis reported multiple intrahepatic metastases, multiple bone metastases over whole body, left lung lower lobe small nodule metastasis pending for confirmation.

2. Composition:

When administered to human subject, YS-ON-001 is formulated in sterile water for injection.

3. Administration regimen:

With consent of patient, from 25 Mar. 2016 onwards YS-ON-001 was administered through intramuscular injection. In the first month, 1 dose (1 ml) was administered every other day. On second month, 1 dose administered each day. On third month, 2 doses daily. From 10th August, 3 doses daily.

4. Results:

In this example, subject administered with the composition of present disclosure showed no obvious side effects. During treatment, patient's symptoms unchanged, disease was stable without further complication. Lower extremity edema caused by the use of Bevacizumab was improved.

Example 16. Therapeutic Effects of the Composition on Endometrial Cancer

1. Subject:

Zhang, female, age 56, diagnosed in December 2010 with third stage endometrial cancer, underwent extensive abdominal hysterectomy+radical ovarian cancer surgery. Postoperative pathology found endometrial adenocarcinoma (histologic tumor grade 1), bilateral ovarian cancer infiltration, right uterosacral ligament metastasis. After surgery, January 2011 onwards started treatment with Docetaxel+Cisplatin chemotherapy. In January 2015 discovered liver and rectal recurrence and metastases, chemotherapy and cancer pain treatment followed.

2. Composition:

When administered to human subject, YS-ON-001 is formulated in sterile water for injection.

3. Administration regimen:

With consent of patient, from 10 Jun. 2016 onwards YS-ON-001 was administered through intramuscular injection. For first 10 days 2 doses (2 ml) daily, subsequently 4 doses (4 ml) daily.

4. Results:

In this example, subject administered with the composition of present disclosure showed no obvious side effects, except from muscular stiffness at injection site. After 2 months treatment, compared to previous month CT examination, lower density lumps on left abdomen wall slightly reduced, obvious irregular thickening on splenic flexure in proximity, slightly better than before.

Example 17. Therapeutic Effects of the Composition on Ovarian Cancer

1. Subject:

Zhou, female, age 56, diagnosed in June 2016 with stage IIIc ovarian cancer (high-grade serous carcinoma), underwent laparotomy for ovarian cancer cytoreductive surgery+ rectal cancer resection. Postoperative pathology report (left uterine appendages, right ovary) matched high-grade serous carcinoma, rectal lesions, cancerous tissues found at appendiceal serosa and abdominal wall.

2. Composition:

When administered to human subject, YS-ON-001 is formulated in sterile water for injection.

3. Administration regimen:

With consent of patient, from 16 Jun. 2016 onwards YS-ON-001 was administered through intramuscular injection. 2 doses (2 ml) daily for first 7 days, followed by 4 doses (4 ml) daily thereafter. At the same time, Docetaxel and Carboplatin was used as combined treatment on doctor's advice.

4. Results:

In this example, subject administered with the composition of present disclosure showed no obvious side effects. During treatment, patient symptoms remained unchanged, stable without further progression.

REFERENCES

Any listing or discussion of an apparently prior-published document in this specification should not necessarily be taken as an acknowledgement that such document is part of the state of the art or is common general knowledge.

The following references may be of interest:

Wanqing Chen, et al. Cancer Statistics in China, 2015. Cancer Journal for Clinicians. 2016 Vol. 66: 115-132.

Guoqian Kuang, et al. Current Status and Prospect of Cancer Virotherapy Clinical Studies. Journal of Guangxi Medical University, 1995 Vol. 12: 617-619.

Shounan Tan, Fengyu Zhang. Studies on Rabies and Rabies Vaccine for Human Use. Medical Information 2011 Vol. 24: 2841-2842.

Yuhui Zhang. The Establishment of Rabies Vaccine Purification Technology. Chinese Journal of Biologicals 1999 Vol. 12 Iss. No. 4: 231-232.

Jiang Zhong. Oncolytic Virus and Tumor Treatment, Foreign Medicine (Microbiology Section), 2004 Vol. 27 Iss. No. 6.

Kenney S, et al. Viruses as oncolytic agents: a new age for therapeutic virus. J Nati Cancer Inst, 1994, 86: 1185.

Lorence, et al. Complete regression of human neuroblastoma xenografts in athymic mice after local Newcastle disease virus therapy. J Nati Cancer Inst, 1994, 86: 1228.

CN100341571C
RU2414238C2
US2010/0297072A1
WO2009/016433

The invention claimed is:

1. A method for treating cancer in a subject, comprising administering to the subject a composition comprising: a) polyinosinic-polycytidylic acid (PIC), b) an antibiotic or a polyamine compound, c) a cation ion selected from the group consisting of calcium, cadmium, lithium, magnesium, cerium, cesium, chromium, cobalt, deuterium, gallium, iodine, iron, zinc, and any combination thereof, and d) a virus; wherein the virus is incapable of replication in a human subject.

2. The method of claim 1, wherein the virus belongs to a family selected from the group consisting of rhabdoviridae, adeniviridae, arenaviridae, astroviridae, bunyaviridae, cliciviridae, flaviviridae, hepatitis delta virus, hepeviridae, mononegavi rales, nidovirales, piconaviridae, orthomyxoviridae, papillomaviridae, parvoviridae, polyomaviridae, poxviridae, reoviridae, retroviridae, and togaviridae.

3. The method of claim 2, wherein the virus belongs to Lyssavirus genus of rhabdoviridae family.

4. The method of claim 3, wherein the virus is a rabies virus.

5. The method of claim 1, wherein the antibiotic is selected from the group consisting of kanamycin, tacrolamycin, anthracycline, butyrin sulphate, gentamicin, hygromycin, amikacin, nebramycin, β-lactam, neomycin, puromycin, streptomycin, streptozocin, and any combination thereof.

6. The method of claim 1, wherein the composition comprises a polyamine compound, wherein the polyamine compound is selected from the group consisting of arginine salt, spermidine, N-(3-aminopropyl), N-(3-aminopropyl)-1,4-butanediamine, spermine, OS-dimethylaminothiophosphate, poly-lysine, aminoglyco side, and any combination thereof.

7. The method of claim 1, wherein cancer comprises lung cancer, breast cancer, thyroid cancer, kidney cancer, gastric adenocarcinoma, liver cancer, melanoma, tongue cancer, colon cancer, rectal cancer, endometrial cancer, pancreatic cancer, prostate cancer, cervical cancer, and ovarian cancer.

8. The method of claim 1, wherein cancer is a metastatic tumor.

9. The method of claim 1, wherein the cancer is not caused by the virus.

10. The method of claim 1, wherein the route of said administration is selected from the group consisting of intramuscular, intraperitoneal, intravenous, subcutaneous, transdermal, intradermal, intranasal, intraocular, oral, sublingual, intratumoral, and peritumoral.

11. The method of claim 1, further comprising treating the subject with an anti-tumor treatment regimen is selected from the group consisting of chemotherapy, radiotherapy, targeted therapy, and immunotherapy.

12. The method of claim 1, wherein the ratio of the virus to the PIC is selected from the group consisting of: 1 IU/50 µg, 1 IU/60 µg, 1 IU 70 µg, 1 IU/80 µg, 1 IU/90 µg, 1 IU/100 µg, 1 IU/125 µg, 1 IU/200 µg, 1 IU/250 µg, 1 IU/300 µg, 1 IU/350 µg, I IU/400 µg, 1 IU/450 µg, 1 IU/500 µg, 1 IU/550 µg, 1 IU/600 µg, 1 IU/700 µg, 1 IU/800 µg, 1 IU/1000 µg, 1 IU/1500 µg, 1 IU/2000 µg, 1 IU/2500 µg, 1 IU/3000 µg, I IU/4000 µg, 1 IU/5000 µg, 1 IU/6000 µg, 1 IU/7000 µg, 1 IU/8000 µg, 1 IU/9000 µg, 1 IU/10,000 µg, and a range between any two of the above ratios.

13. The method of claim 1, wherein the ratio of the virus to the PIC 1 IU/500 µg.

14. The method of claim 1, wherein amount of the PIC is between from 250 µg to 5000 µg per unit dose.

15. The method of claim 1, wherein amount of the PIC is selected from the group consisting of 250 µg, 500 µg, 1000 µg, 1500 µg, 2000 µg, 3000 µg, 4000 µg, and 5000 µg per unit dose.

16. The method of claim 1, wherein the amount of the virus is selected from the group consisting of 0.5 IU, 1.0 IU, 1.5 IU, 2.0 IU, 2.5 IU, 3.0 IU, 3.5 IU, 4.0 IU, 5.0 IU, 6.0 IU, 7.0 IU, 8.0 IU, 9.0 IU, 10.0 IU, 15.0 IU, 20.0 IU, 30.0 IU, 40.0 IU, 50.0 IU, 60.0 IU, 70.0 IU, 80.0 IU, 90.0 IU, 100.0 IU per unit dose, and a range between any two of the above amounts.

17. The method of claim 1, wherein the amount of the virus is between from 1.0 IU to 5.0 IU per unit dose.

18. The method of claim 17, wherein the unit dose is prepared into a volume which is selected from the group consisting of 0.1 ml, 0.15 ml, 0.2 ml, 0.5 ml, 1.0 ml, 1.5 ml, 2.0 ml, 2.5 ml, 3.0 ml, 4.0 ml, 5.0 ml, 10.0 ml, 20.0 ml, 30.0 ml, 40.0 ml, 50.0 ml, 60.0 ml, 70.0 ml, 80.0 ml, 90.0 ml, 100.0 ml, 150.0 ml, 200.0 ml, 250.0 ml, and a range between any two of the above volumes.

19. The method of claim 1, wherein cancer is breast cancer.

20. The method of claim 1, wherein cancer is liver cancer.

* * * * *